United States Patent [19]
Chiba et al.

[11] Patent Number: 6,004,565
[45] Date of Patent: Dec. 21, 1999

[54] COMPOSITIONS AND METHODS OF USING COMPOSITIONS WITH ACCELERATED LYMPHOCYTE HOMING IMMUNOSUPPRESSIVE PROPERTIES

[75] Inventors: Kenji Chiba; Kunitomo Adachi, both of Fukuoka, Japan

[73] Assignee: Yoshitomi Pharmaceutical Industries, Ltd., Osaka, Japan

[21] Appl. No.: 08/933,738

[22] Filed: Sep. 23, 1997

[30] Foreign Application Priority Data

Sep. 2, 1997 [JP] Japan .................................. 9-237273

[51] Int. Cl.$^6$ .............................................. A61K 31/135
[52] U.S. Cl. .................... 424/278.1; 514/487; 514/546; 514/653; 560/29; 560/163; 564/223; 564/355
[58] Field of Search .................... 564/223, 355; 560/29, 163; 514/653, 487, 546; 424/278.1

[56] References Cited

U.S. PATENT DOCUMENTS

| | | | |
|---|---|---|---|
| 5,037,958 | 8/1991 | Hashimoto | 530/350 |
| 5,219,884 | 6/1993 | Fugita | 514/472 |
| 5,604,229 | 2/1997 | Fujita et al. . | |
| 5,686,479 | 11/1997 | Okumoto | 514/383 |
| 5,719,175 | 2/1998 | Fugita | 514/440 |

FOREIGN PATENT DOCUMENTS

PCT/JP95/
01654 8/1995 Japan .

OTHER PUBLICATIONS

P. Cresswell, "Assembly, Transport, and Function of MHC Class II Molecules," *Annu. Rev. Immunol.*, vol. 12, pp. 259–293 (1994).

M.R. Jackson et al., "Assembly and Intracellular Transport of MHC Class I Molecules," *Annu. Rev. Cell Biol.*, vol. 9, pp. 207–235 (1993).

J.C. Howard, "Supply and transport of peptides presented by class I MHC molecules," *Curr. Opin. Immunol.*, vol. 7, pp. 69–76 (1995).

B.D. Kahan, "Medical Intelligence, Drug Therapy, Cyclosporine," *The New England Journal of Medicine*, vol. 321, No. 25, pp. 1725–1738 (Dec. 21, 1989).

J. Fung et al., "A Randomized Trial of Primary Liver Transplantation Under Immunosuppression with FK 506 vs Cyclosporine," *Transplantation Proceedings*, vol. 23, No. 6, pp. 2977–2983 (Dec. 1991).

J.F. Borel et al., "Biological Effects of Cyclosporin A: A New Antilymphocytic Agent," *Agents and Actions*, vol. 6/4, pp. 468–475 (1976).

J. F. Borel, "Pharmacology of Cyclosporine (Sandimmune) IV. Pharmacological Properties in Vivo," *Pharmacological Reviews*, vol. 41, No. 3, pp. 259–371 (1989).

T. Kino et al., "FK–506, A Novel Immunosuppressant Isolated from a Streptomyces, I. Fermentation, Isolation and Physico–Chemical and Biological Characteristics," *The Journal of Antibiotics*, vol. 40, No. 9, pp. 1249–1255 (1987).

T. Kino et al., "FK–506, A Novel Immunosuppressant Isolated from a Streptomyces, II. Immunosuppressive Effect of FK–506 In Vitro," *The Journal of Antibiotics*, vol. 40, No. 9, pp. 1256–1265 (Sep. 1987).

N. Inamura et al., "Prolongation of Skin Allograft Survival in Rats by a Novel Immunosuppressive Agent, FK506," *Transplantation*, vol. 45, No. 1, pp. 206–209 (Jan. 1988).

J. Liu et al., "Calcineurin Is a Common Target of Cyclophilin–Cyclosporin A and FKBP–FK506 Complexes," *Cell*, vol. 66, pp. 807–815, (Aug. 23, 1991).

Y. Kokado et al., "Low–dose ciclosporin mizoribine and prednisolone in renal transplantation: A New triple–drug therapy," *Clin. Transplantation*, vol. 4, pp. 191–197 (1990).

T. Fujita et al., "Fungal Metabolites, Part 11. A Potent Immunosuppressive Activity Found in *Isaria sinclairii* Metabolite," *The Journal of Antibiotics*, vol. 47, No. 2, pp. 208–215 (Feb. 1994).

T. Fujita et al., "Fungal Metabolites, Part 12. Potent Immunosuppressant, 14–Deoxomyriocin, (2S, 3R, 4R)—(E) – 2–Amino–3, 4–Dihydroxy–2–Hydroxymethyleicos–6–Enoic Acid and Structure–Activity Relationships of Myriocin Derivatives," *The Journal of Antibiotics*, vol. 47, No. 2, pp. 216–224 (Feb. 1994).

S. Sasaki et al., "Fungal Metabolites. Part 14. Novel Potent Immunosuppressants, Mycestericins, Produced by *Mycelia sterilia*," *The Journal of Antibiotics*, vol. 47, No. 4, pp. 420–433 (Apr. 1994).

H.ff.S. Davies et al., "Long–Term Survival of Kidney Allografts in Dogs After Withdrawal of Immunosuppression with Ciclosporin and Azathioprine," *Eur. Surg. Res.*, vol. 21, pp. 65–75 (1989).

H. Amemiya et al., "Synergistic Effect of Cylcosporine and Mizoribine on Survival of Dog Renal Allografts," *Transplantation*, vol. 46, No. 5, pp. 768–771 (Nov. 1988).

M.L. Arbonés et al., "Lymphocyte Homing and Leukocyte Rolling and Migration are Impaired in L–Selectin–Deficient Mice," *Immunity*, vol. 1, pp. 247–260 (Jul. 1994).

(List continued on next page.)

*Primary Examiner*—David Saunders
*Assistant Examiner*—Mary Beth Tung
*Attorney, Agent, or Firm*—Evenson, McKeown Edwards & Lenahan P.L.L.C.

[57] ABSTRACT

The methods and compositions of the invention and the compounds used in the invention involve a novel immunosuppression mechanism, accelerated lymphocyte homing immunosuppression (ALH-immunosuppression). For example, the compound FTY720 specifically directs lymphocytes to the peripheral lymph nodes, mesenteric lymph nodes, and Peyer's patches. By reversibly sequestering lymphocytes in these tissues, the compounds can inhibit an immune response in a mammal. Understanding these mechanisms provides a novel immunosuppression therapy that can synergistically interact with other immunosuppressive compounds. Screening methods for identifying similar ALH-immunosuppression compounds are also described. The invention allows better treatments and therapies wherever an immunosuppression regimen is desired.

6 Claims, 11 Drawing Sheets

OTHER PUBLICATIONS

A. Hamann et al., "Role of $\alpha_4$–Integrins in Lymphocyte Homing to Mucosal Tissues in Vivo," *Journal of Immunology*, vol. 152, pp. 3282–3293 (1994).

Y. Imai et al., "Sulphation requirement for GlyCAM–1, an endothelial ligand for L–selectin," *Nature*, vol. 361, pp. 555–557 (Feb. 11, 1993).

T. B. Issekutz, "Inhibition of In Vivo Lymphocyte Migration to Inflammation and Homing to Lymphoid Tissues by the TA–2 Monoclonal Antibody," *The Journal of Immunology*, vol. 147, No. 12, pp. 4178–4184 (Dec. 15, 1991).

C. Berlin et al., "$\alpha 4\beta 7$ Integrin Mediates Lymphocyte Binding to the Mucosal Vascular Addressin MadCAM–1," *Cell*, vol. 74, pp. 185–195 (Jul. 16, 1993).

B.D. Kahan et al., "Preclinical Evaluation of a New Potent Immunosuppressive Agent, Rapamycin," *Transplantation*, vol. 52, No. 2, pp. 185–191 (Aug. 1991).

R. Schwartz et al., "Drug–induced Immunological Tolerance," *Nature*, vol. 183, p. 1682 (Jun. 13, 1959).

L.A. Turka et al., "Guanine Ribonucleotide Depletion Inhibits T Cell Activation," *J. Clin. Invest.*, vol. 87, pp. 940–948 (Mar. 1991).

W.A. Lee et al., "Bioavailability Improvement of Mycophenolic Acid Through Amino Ester Derivatization," *Pharmaceutical Research*, vol. 7, No. 2, pp. 161–166 (1990).

D.V. Cramer et al., "The Effect of a New Immunosuppressive Drug, Brequinar Sodium, on Heart, Liver, and Kidney Allograft Rejection in the Rat," *Transplantation*, vol. 53, No. 2, pp. 303–308 (Feb. 1992).

L.J. Picker et al., "Physiological and Molecular Mechanisms of Lymphocyte Homing," *Ann. Rev. Immunol.*, vol. 10, pp. 561–591 (1992).

J.E. Miller et al., "A New Model of Heterotopic Rat Heart Transplantation with Application for In Vivo $^{31}$P Nuclear Magnetic Resonance Spectroscopy," *Transplantation*, vol. 39, No. 5, pp. 555–558 (May 1985).

M.J. Dallman et al., "Cytokine Gene Expression: Analysis using Northern Blotting, Polymerase Chain Reaction and in situ Hybridization," *Immunological Reviews*, No. 119, pp. 163–179 (1991).

M.J. Dallman et al., "Cytokine Gene Transcription in Vascularised Organ Grafts: Analysis Using Semiquantitative Polymerase Chain Reaction," *J. Exp. Med.*, vol. 174, pp. 493–496 (Aug. 1991).

J. Wang et al., "Local Hormone Networks and Intestinal T Cell Homeostasis," *Science*, vol. 275, pp. 1937–1939 (Mar. 28, 1997).

European FK506 Multicentre Liver Study Group, "Randomised trial comparing tacrolimus (FK506) and cyclosporin in prevention of liver allograft rejection", *The Lancet*, vol. 344, pp. 423–428 (Aug. 13, 1994).

T. Tanaka et al., "Characterization of a CD3–like Rat T Cell Surface Antigen Recognized by a Monoclonal Antibody," *The Journal of Immunology*, vol. 142, No. 8, pp. 2791–2795 (Apr. 15, 1989).

G.R. Woollett et al., "Molecular and antigenic heterogeneity of the rat leukocyte–common antigen from thymocytes and T and B lymphocytes," *Eur. J. Immunol.*, vol. 15, pp. 168–173 (1985).

Y. Masaki et al., "Microchimerism and Heart Allograft Acceptance," *Transplantation Proceedings*, vol. 27, No. 1, pp. 148–150 (Feb. 1995).

C. Legendre et al., "Prediction of Successful Allograft Rejection Retreatment with OKT3," *Transplantation*, vol. 53, No. 1, pp. 87–90 (Jan. 1992).

T. Tamatani et al., Characterization of rat LECAM–1 (L–selectin) by the use of monoclonal antibodies and evidence for the presence of soluble LECAM–1 in rat sera, *Eur. J. Immunol.*, vol. 23, pp. 2181–2188, (1993).

L.M. McEvoy et al., "Anti–CD43 inhibition of T Cell homing," *J. Exp. Med.*, vol. 185, No. 8, pp. 1493–1498 (Apr. 21, 1997) (Abstract only).

T. Tamatani et al., "Characterization of the rat leukocyte integrin, CD11/CD18, by the use of LFA–1 subunit–specific monoclonal antibodies," *Eur. J. Immunol.*, vol. 21, pp. 627–633 (1991).

A. Siegling et al., "A novel multispecific competitor fragment for quantitative PCR analysis of cytokine gene expression in rats," *Journal of Immunological Methods*, vol. 177, pp. 23–28 (1994).

Copending U.S. Application Serial No. 08/801,390, filed Feb. 20, 1997.

Tetsuro Fujita et al., "Simple Compounds, 2–alkyl–2–amino–1,3–propanediols Have Potent Immunosuppressive Activity", *BioMed. Chem. Lett.*, vol. 5, No. 8, pp. 847–852 (1995).

T. Fujita et al., "Potent Immunosuppressants, 2–alkyl–2–aminopropane–1,3–diols", *J. Med. Chem.*, vol. 39, pp. 4451–4459 (1996).

Kunitomo Adachi et al., "Design, Synthesis, And Structure––Activity Relationships of 2–substituted–2–amino–1,3–propanediols: Discovery of a Novel Immunosuppressant, FTY720", *BioMed. Chem. Lett.*, vol. 5, No. 8, pp. 853–856 (1995).

K. Chiba et al., "FTY720, A Novel Immunosuppressant Possessing Unique Mechanisms. I. Prolongation of Skin Allograft Survival and Synergistic Effect in Combination with Cyclosporine in Rats", *Transplant. Proc.*, vol. 28, No. 2, pp. 1056–1059 (1996).

Barry D. Kahan et al., "The Synergistic Interactions In Vitro and In Vivo of Brequinar Sodium with Cyclosporine or Rapamycin aAone and in Triple Combination", *Transplantation*, vol. 55, No. 4, pp. 894–900 (1993).

Y. Hoshino et al., "FTY720, A Novel Immunosuppressant Possessing Unique Mechanisms. II. Long–Term Graft Survival Induction in Rat Heterotopic Cardiac Allografts and Synergistic Effect in Combination with Cyclosporine A", *Transplant. Proc.*, vol. 28, No. 2, pp. 1060–1061 (1996).

T. Kawaguchi et al., "FTY720, A Novel Immunosuppressant Possessing Unique Mechanisms. III. Synergistic Prolongation of Canine Renal Allograft Survival in Combination With Cyclosporine A", *Transplant. Proc.*, vol. 28, No. 2, pp. 1062–1063 (1996).

Seiichi Suzuki et al., "A Novel Immunosuppressant, FTY720, With A Unique Mechanism of Action, Induces Long–Term Graft Acceptance in Rat and Dog Allotransplantation", *Transplantation*, vol. 61, No. 2, pp. 200–205 (1996).

S. Suzuki et al., "Long–Term Graft Acceptance in Allografted Rats and Dogs by Treatment With a Novel Immunosuppressant, FTY720", *Transplant. Proc.*, vol. 28, No. 3, pp. 1375–1376 (1996).

Y. Masubuchi et al., "FTY720, A Novel Immunosuppressant, Possessing Unique Mechanisms. IV. Prevention of Graft Versus Host Reactions in Rats", *Transplant. Proc.*, vol. 28, No. 2, pp. 1064–1065 (1996).

F. Shanahan, "A Gut Reaction: Lymphoepithelial Communication in the Intestine", *Science,* vol. 275, pp. 1897–1898 (1997).

C. Legendre et al., "Prediction of Successful Allograft Rejection Retreatment With OKT3", *Transplantation,* vol. 53, pp. 94–94 (1992).

Hirose, R, et al., Bioorgan. Med. Chem. Let. 6(22)2647–2650, 1996.

Fujita, T., et al., Bioorgan. Med. Chem. Let. 5(16)1857–1860, 1995.

Chiba, K. Adachi, K. Drugs of the Future. 22(1)18–22, Mar. 26, 1997.

Suzuki, S. et al., Transplant. Proc. 28(4)2049–2050, Apr. 1996.

Enosawa, S., et al., Immunopharmacology 34:171–179, 1996.

Suzuki, S., et al., Immunology. 89:518–523, 1996.

M. Slapak et al., "The Use of Low–Dose Cyclosporine in Combination With Azathioprine and Steriods in Renal Transplantation," *Transplantation Proceedings,* vol. XVII, No. 1, Feb. 1985, pp. 1222–1226.

COMPOSITIONS AND METHODS OF USING COMPOSITIONS WITH ACCELERATED LYMPHOCYTE HOMING IMMUNOSUPPRESSIVE PROPERTIES

BACKGROUND OF THE INVENTION

1. Field of the Invention

This invention relates to the chemistry and biology of compounds with immunosuppressive and lymphocyte homing activities and, more specifically, this invention relates to methods and comprises compositions for accelerating lymphocyte homing in a mammal.

2. Description of Related Art

In general, compounds used to suppress the immune response attack certain immune cells. By either removing these cells from the immune system or hampering their ability to respond to chemical messengers, the number of cells participating in any immune response decreases. With fewer cells responding, the immune system cannot mount the same response reaction. The result is immunosuppression.

The use of these compounds follows directly from our understanding of the immune response and the function of immune cells. Numerous publications in the art describe the molecular and cellular aspects of the immune response. Generally, the immune system responds to an antigen first by processing and presenting the antigen through antigen presenting cells (APCs). Over the last decade, intensive research has resulted in a deep and detailed knowledge of this process at the molecular level (1–3). Following the APCs action are the T lymphocytes or T cells. Activated by a process involving antigen presentation by the APC, T cells then initiate the development of a variety of effector immune cells. The activities of phagocytes, natural killer cells, cytotoxic T cells, and B cells and other effector cells each arise from the cytokines secreted from activated T cells. The cytokines, then, are the chemical messengers that trigger the immune response mechanisms that the effector cells perform.

By killing or modifying the cells or messengers of the immune system, certain compounds can be used as treatments and therapies for suppressing the immune response. Our understanding of the immune response has led to two general groups of immunosuppressive compounds, those compounds effecting cytokine action and those directly effecting immune cell metabolism and activity.

In the first group are cyclosporin A (CsA), tacrolimus (TRL) and rapamycin (4-5). CsA, a cyclic peptide, is produced from the Trichoderma polysporum fungus (6-7). TRL, or FK-506, is a macrolide from *Streptomyces tsukubaensis* (8–10). These compounds cut out the cytokine messengers of the immune response by preventing their synthesis. The immune effector cells, therefore, cannot be recruited to complete the immune response. Rapamycin, on the other hand, blocks the cytokine signal from effecting the immune cells (34).

More specifically, CsA suppresses the immune response by inhibiting production of the cytokine interleukin 2 (IL-2) in antigen-stimulated helper T cells, a subset of T cells. TRL inhibits antigen-induced T cell proliferation by inhibiting IL-2 production in helper T cells. CsA and TRL act by binding to two different proteins (11), called cyclophilin and FKBP respectively. After the binding, both of the CsA/cyclophilin and TRUFKBP complexes inhibit the phosphatase activity of a protein called calcineurin, which activates nuclear factor (NF-AT) in activated T cells. NF-AT promotes IL-2 gene transcription and thus IL-2 production. However, when the CsA/cyclophilin and TRLUFKBP complexes inhibit activation of NF-AT, production of IL-2 is also inhibited.

Since CsA and TRL have almost the same mechanism of action, these drugs also show quite similar side effects, such as renal and liver toxicity (12). Multiple drug therapies with either CsA or TRL, using steroids or other immunosuppressants such as azathioprine and mizoribine (13–14), were widely used in order to reduce the side effects of individual immunosuppressants. However, the similar side effects of CsA and TRL prohibits their use together. New immunosuppressant compounds should not only be highly safe but should also possess a mechanism of action distinct from CsA and TRL so that they can be concomitantly administered.

Compounds from the second group of similarly-acting chemicals each interfere with nucleoside synthesis in the immune cells, arresting their metabolism and their immune activity. The group includes azathioprine (35), mizoribine (36), mycophenolic acid (37), and brequinar sodium (38). These compounds can also result in toxic side effects.

Researchers and clinicians use these compounds in human therapies. Those employing CsA have made great contributions to the prevention of acute rejection in human organ transplantation. Immunosuppressants are also used to treat autoimmune diseases, such as rheumatoid arthritis, and diseases such as psoriasis, atopic dermatitis, bronchial asthma, and pollinosis. However, because of the toxic side effects of the currently used compounds, new, more effective and less toxic methods to suppress the immune response are needed in the art.

SUMMARY OF THE INVENTION

The instant invention involves compositions and methods that suppress the immune response in mammals in a novel way. This immunosuppression results from accelerating lymphocyte homing, for example to any of the mesenteric or peripheral lymph tissues or Peyer's patches. This new activity, accelerated lymphocyte homing immunosuppression (ALH-immunosuppression), can be used in conjunction with other immunosuppressive therapies or compounds while avoiding dangerous or toxic side effects. The present invention provides new and useful methods, therapies, treatments, and compositions wherever immunosuppression is desired or manipulating lymphocyte populations is desired. For example, the invention can be used in therapies or treatments for preventing rejection in organ or cell transplantation, genetically modified cell therapy, ex vivo gene therapy, or other cell therapy methods. Research and development may provide additional or related uses directed to the intestinal immune system and the maintenance or manipulation of intestinal intraepithelial lymphocyte function. Thus, the ALH-immunosuppressive compositions of the invention can be used to direct or redirect lymphocytes within a mammal. Such uses do not necessarily require an immunosuppressive action.

In one embodiment, the invention provides a method of suppressing the immune response by accelerating lymphocyte homing to any of the mesenteric or peripheral lymph tissues or Peyer's patches. This embodiment can be used to suppress the immune response in a mammal and comprises administering an ALH-immunosuppressive compound. The ALH-immunosuppressive compounds of this invention functionally act by directing lymphocytes to specific locations or lymphoid tissues. This lymphocyte homing activity can be reversible, so that suspending treatment restores normal lymphocyte populations. The compounds may also act to selectively decrease populations of certain lymphocytes in blood or lymph tissue, such as specifically decreasing populations of circulating lymphocytes or spleen lymphocytes.

Structurally, the class of ALH-immunosuppressive compounds derives from myriocin or ISP-1, a natural product of *Isaria sinclairii* (15). Myriocin is depicted below.

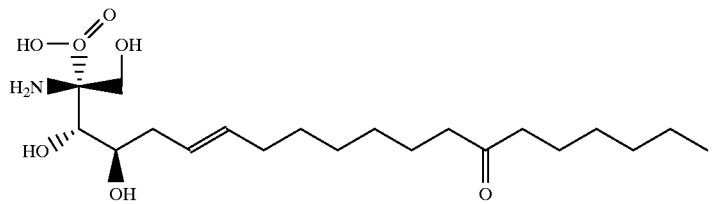

Numerous homologs, analogs or derivatives of these compounds can be prepared by methods known in the art, such as described in the references, particularly (17), which is specifically incorporated herein by reference. In general, for this invention, the ALH-immunosuppressive compounds can be 2-aminopropane-1,3-diol compounds, according to the following formula:

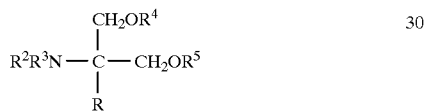

wherein R is an optionally substituted straight or branched carbon chain, an optionally substituted aryl, an optionally substituted cycloalkyl or the like;

and R2, R3, R4, and R5 are the same or different and each is a hydrogen, an alkyl, an acyl, or an alkoxycarbonyl, or R4 and R5 may be bonded to form an alkylene chain, which may be substituted by alkyl, aryl, or an alkoxycarbonyl.

Also, for this invention, the ALH-immunosuppressive compounds can be bezene compounds, of the formula:

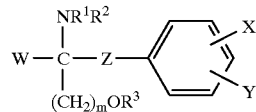

wherein W is hydrogen; a straight or branched chain alkyl having 1 to 6 carbon atoms; a straight or branched chain alkenyl having 2 to 6 carbon atoms; a straight or branch chain alkynyl having 2 to 6 carbon atoms; a phenyl, which may be substituted by hydroxy; $R4(CH2)_n$; or a straight or branched chain C1–C6 alkyl substituted by 1 to 3 substituents selected from the group consisting of a halogen, a cycloalkyl, and a phenyl, which may be substituted by hydroxy;

X is hydrogen, a straight-chain alkyl having carbon atoms in the number of p or a straight-chain alkoxy having carbon atoms in the number of (p−1), wherein the straight-chain alkyl having carbon atoms in the number of p and the straight-chain alkoxy having carbon atoms in the number of (p−1) may have 1 to 3 substituents selected from the group consisting of an alkyl, hydroxy, an alkoxy, an acyloxy, amino, an akylamino, an acylamino, oxo, a haloalkyl, a halogen, and a phenyl, which may have a substituent, and wherein the phenyl, which may have a substituent, may have 1 to 3 substituents selected from the group consisting of an alkyl, hydroxy, an alkoxy, an acyl, an acyloxy, amino, an alkylamino, an acylamino, a holalkyl, and a halogen;

Y is hydrogen, an alkyl, hydroxy, an alkoxy, an acyl, an acyloxy, amino, an alkylamino, an acylamino, a haloalkyl, or a halogen;

Z is a single bond or a straight-chain alkylene having carbon atoms in the number of q;

p and q are the same or different and each is an integer of 1 to 20, with the proviso that $6 \leq p+q \leq 23$;

m is 1, 2, or 3;

n is 2 or 3;

R1 and R2 are the same of different and each is hydrogen, an alkyl or an acyl;

R3 is hydrogen, an alkyl or an acyl;

and R4 is hydrogen, an alkyl or an acyl, where the benzene compounds can be optically active isomers of the above and salts of the compounds.

A disclosure of specific compounds, substituent groups, and variations included in the ALH-immunosuppressive compounds of this invention can be found in U.S. Pat. No. 5,604,229, copending U.S. application Ser. No. 08/801,390, filed Feb. 20, 1997, and PCT application PCT/JP95/01654, filed Aug. 22, 1995. These documents also describe methods to produce and isolate specific compounds that can be used according to this invention. Also, the references (particularly, 18–20) describe methods for producing these compounds. The entire contents of each of these patent documents and references are specifically incorporated by reference into this disclosure and can be relied on to make or isolate the compounds and practice this invention. The homologs, analogs, or derivatives prepared can be tested, by one skilled in the art, to ensure that they possess ALH-immunosuppressive activity, as described below. Furthermore, the compounds can be prepared or isolated as any of a number of pharmaceutically or physiologically acceptable salts or be prepared as optically active isomers of any of the described compounds.

One preferred structural embodiment of the ALH-immunosuppressive compounds used in the invention is the synthetic product FTY720, 2-amino-2[2-(4-octylphenyl) ethyl]propane-1,3-diol hydrochloride, shown below.

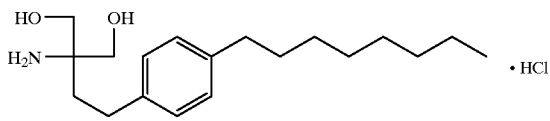

In other embodiments, the invention provides a method of accelerating lymphocyte homing in a mammal, where a ALH-immunosuppressive composition is used. The composition comprises a 2-aminopropane-1,3-diol compound and/or a benzene compound. In these embodiments, after being administering the composition, the mammal's immune cells maintain their IL-2-producing ability or that ability is not significantly reduced by the action of the ALH-immunosuppressive composition.

In another embodiment, the invention provides a method for reversibly reducing the number of circulating immune cells in a mammal. These embodiments comprise introducing an ALH- immunosuppressive composition, such as one containing a 2-aminopropane-1,3-diol compound or a homolog or analog thereof, or a benzene compound, or a homolog or analog thereof, to the mammal. A measurable amount of the circulating immune cells are directed to peripheral or mesenteric lymph tissue. In a related aspect, the invention provides a method for manipulating lymphocyte traffic in a mammal comprising administering an ALH-immunosuppressive composition.

By manipulating lymphocyte traffic or reducing circulating lymphocytes, the number of lymphocytes in a particular tissue changes compared to control levels. The examples below indicate changes in lymphocyte numbers for a variety of tissues as well as circulating blood. However, the numbers in the examples do not limit the degree of change in the lymphocyte numbers required. The degree of change can also be any change in lymphocyte numbers that is reasonably attributable to a shift from the control levels as a result of the ALH-immunosuppressive composition or the methods described herein. Alternatively, the degree of change can be those that result in a measurable difference in the immune response of the mammal as determined by any number of assays that one skilled in the art may employ. Also, manipulating lymphocyte traffic or reducing lymphocyte levels in a particular tissue can be determined by following labeled lymphocytes. Changes in the tissue location, the frequency of lymphocyte visits to a tissue, or the numbers of lymphocytes at a specific time period following administration of the labeled lymphocytes, and comparison to control, indicates a manipulation of lymphocyte traffic or a reduction in lymphocyte levels.

In these aspects, an ALH-immunosuppressive composition may also be administered with an antibody, though not necessarily at the same time. Generally, the antibody will be directed against a lymphocyte or an antigen that is involved with the lymphocyte homing process. Numerous antibodies of that type are known in the art. These aspects of the invention can provide, for example, important animal models. The animal models can be used to develop therapies employing the immune system, or its components, or for identifying novel immuno-active compounds or compounds that are involved in the immune response.

In another aspect, the invention relates to a method for identifying the presence or absence of ALH-immunosuppressive activity in a sample, which comprises administering a sample to a mammal and assaying the survival of transplanted tissue or cells in the mammal. By measuring and comparing the ratio of lymphocytes in circulating blood versus lymphocytes in peripheral or mesenteric lymph nodes, before and after treatment, any ALH-immunosuppressive activity can be identified. In these methods, rodents such as rats and mice, may be used and transplanted tissue or cells can be heart, kidney, or skin tissue. Also, for this aspect of the invention, populations of pre-labeled lymphocytes can be introduced into a mammal and detected following administration of a sample. Certain patterns of lymphocyte homing can result when the sample contains ALH-immunosuppressive activity.

In yet another aspect, the invention relates to ALH-immunosuppressive compositions and methods employing these compositions. These compositions comprise a 2-aminopropane-1,3-diol compound, or a homolog or analog thereof, and/or a benzene compound, or a homolog or analog thereof. These compositions can be combined with one or more other immunosuppressive compounds, such as cyclosporin, azathioprine, tacrolimus, mycophenolate mofetil, or analogs or derivatives of these compounds, or steroids, or any other immunosuppressive compound. Because the mechanism of action of the ALH-immunosuppressive activity does not result in similar side effects as in many widely used immunosuppressive compounds, these compositions provide novel synergistic actions, which may allow reduced therapeutic doses.

The ALH-immunosuppressive compositions of this aspect of the invention show superior immunosuppressive effects and are useful themselves, or in methods, for the prevention or treatment of various indications such as immunosuppression in organ, cell, or bone marrow transplantation, various autoimmune diseases or various allergy diseases. Namely, the compositions of the present invention have pharmacological activities such as immunosuppressive activity or antimicrobial activity and therefore are useful for the prevention or treatment of resistance to transplantation or transplantation rejection of organs or tissues (such as heart, kidney, liver, lung, bone marrow, cornea, pancreas, intestinum tenue, limb, muscle, nervus, fatty marrow, duodenum, skin or pancreatic islet cell etc., including xeno-transplantation), graft-versus-host diseases by bone marrow transplantation, autoimmune diseases such as rheumatoid arthritis, systemic lupus erythematosus, nephrotic syndrome lupus, Hashimoto's thyroiditis, multiple sclerosis, myasthenia gravis, type I diabetes mellitus, type II adult onset diabetes mellitus, uveitis, nephrotic syndrome, steroid-dependent and steroid-resistant nephrosis, palmoplantar pustulosis, allergic encephalomyelitis, glomerulonephritis, etc., and infectious diseases caused by pathogenic microorganisms.

The compositions of the present invention are useful in methods for treating inflammatory, proliferative and hyperproliferative skin diseases and cutaneous manifestations of immunologically-mediated illnesses such as psoriasis, psoriatic arthritis, atopic eczema (atopic dermatitis), contact dermatitis and further eczematous dermatitises, seborrheic dermatitis, lichen planus, pemphigus, bullous pemphigoid, epidermolysis bullosa, urticaria, angioedemas, vasculitides, erythemas, cutaneous eosinophilias, acne, alopecia areata, eosinophilic fasciitis, and atherosclerosis.

More particularly, the compositions of the present invention are useful in methods for hair revitalizing, such as in the treatment of female or male pattern alopecia, or senile alopecia, by providing epilation prevention, hair germination, and/or a promotion of hair generation and hair growth.

The compositions of the present invention are further useful in methods for the treatment of respiratory diseases, for example, sarcoidosis, fibroid lung, idiopathic interstitial pneumonia, and reversible obstructive airways disease, including conditions such as asthma, including bronchial asthma, infantile asthma, allergic asthma, intrinsic asthma, extrinsic asthma and dust asthma, particularly chronic or inveterate asthma (for example late asthma and airway hyperreponsiveness), bronchitis and the like.

The compositions of the present invention may also be useful in methods for treating hepatic injury associated with ischemia.

The compositions of the present invention are also indicated in certain methods for treating eye diseases such as conjunctivitis, keratoconjunctivitis, keratitis, vernal conjunctivitis, uveitis associated with Behcet's disease, herpetic keratitis, conical cornea, dystorphia epithelialis corneae, keratoleukoma, ocular pemphigus, Mooren's ulcer, scleritis, Graves' ophthalmopathy, severe intraocular inflammation and the like.

The compositions of the present invention are also useful in methods for preventing or treating inflammation of mucosa or blood vessels (such as leukotriene $B_4$-mediated diseases, gastric ulcers, vascular damage caused by ischemic diseases and thrombosis, ischemic bowel disease, inflammatory bowel disease (e.g. Crohn's disease and ulcerative colitis) necrotizing enterocolitis), or intestinal lesions associated with thermal burns.

Further, the compositions of the present invention are also useful in methods for treating or preventing renal diseases including interstitial nephritis, Goodpasture's syndrome, hemolytic uremic syndrome and diabetic nephropathy; nervous diseases selected from multiple myositis, Guillain-Barre syndrome, Ménière's disease and radiculopathy; endocrine diseases including hyperthyroidism and Basedow's disease; hematic diseases including pure red cell aplasia, aplastic anemia, hypoplastic anemia, idiopathic thrombocytopenic purpura, autoimmune hemolytic anemia, agranulocytosis and anerythroplasia; bone diseases including osteoporosis; respiratory diseases including sarcoidosis, fibroid lung and idiopathic interstitial pneumonia; skin diseases including dermatomyositis, vitiligo vulgaris, ichthyosis vulgaris, photoallergic sensitivity and cutaneous T cell lymphoma; circulatory diseases including arteriosclerosis, aortitis, polyarteritis nodosa and myocardosis; collagen disease including scleroderma, Wegener's granuloma and Sjögren's syndrome; adiposis; eosinophilic fasciitis; periodontal disease; nephrotic syndrome; hemolytic uremic syndrome; and muscular dystrophy.

Further, the compositions of the present invention are indicated in the treatment of diseases including intestinal inflammations or allergies such as Coeliac disease, proctitis, eosinophilic gastroenteritis, mastocytosis, Crohn's disease or ulcerative colitis; and food related allergic diseases which have symptomatic manifestation remote from the gastrointestinal tract, for example migraine, rhinitis and eczema.

The compositions of the present invention also have liver regenerating activity and/or activity in promoting hypertrophy and hyperplasia of hepatocytes. Therefore, they are useful in methods for the treatment and prevention of hepatic diseases such as immunogenic diseases (e.g. chronic autoimmune liver diseases including autoimmune hepatitis, primary biliary cirrhosis and sclerosing cholangitis), partial liver resection, acute liver necrosis (e.g. necrosis caused by toxins, viral hepatitis, shock or anoxia), B-virus hepatitis, non-A/non-B hepatitis, and cirrhosis. The compositions of the present invention are also indicated for use as antimicrobial agents, and thus may be used in methods for the treatment of diseases caused by pathogenic microorganisms and the like.

Further, the compositions of the present invention can be used in the prevention or treatment of malignant rheumatoid arthritis, amyloidosis, fulminant hepatitis, Shy-Drager syndrome, pustular psoriasis, Behçet's disease, systemic lupus erythematosus, endocrine opthalmopathy, progressive systemic sclerosis, mixed connective tissue disease, aortitis syndrome, Wegener's gramulomatosis, active chronic hepatitis, Evans syndrome, pollinosis, idiopathic hypoparathyroidism, Addison disease (autoimmune adrenalitis), autoimmune orchitis, autoimmune oophoritis, cold hemagglutinin, paroxysmal cold hemoglobinuria, pernicious anemia, adult T cell leukemia, autoimmune atrophic gastritis, lupoid hepatitis, tubulointerstitial nephritis, membranous nephritis, amyotrophic lateral sclerosis, rheumatic fever, postmyocardial infarction syndrome and sympathetic ophthalmitis.

The compositions of the present invention have antifungal effect and are useful as a antifungal agent.

When the compositions are used as pharmaceuticals or in pharmaceutical or pharmacological methods, an effective amount of the 2-aminopropane-1,3-diol compound or a homolog or analog thereof and/or the benzene compound, or a homolog or analog thereof, is generally admixed with carrier, excipient, diluent and so on and formulated into powders, capsules, tablets, injections, topical administration preparations, or the like, for administering to patients. A lyophilized preparation may be produced by a method known in the art.

While the dose of the compounds used in the compositions varies depending on disease, symptom, body weight, sex, age, and so on, they may be administered, for example, to an adult daily by 0.01–10 mg (potency) in a single dose or in several divided doses, for example when suppressing rejection in kidney transplantation.

Moreover, the compositions of the present invention can be used to suppress the immune system, such as suppressing rejection in organ, cell, or bone marrow transplantation. The compositions can comprise combinations with other immunosuppressant(s), steroid(s) (prednisolone, methylprednisolone, dexamethasone, hydrocortisone and the like) or nonsteroidal anti-inflammatory agent(s). Preferred combinations comprise one or more immunosuppressants such as azathiprine, brequinar sodium, deoxyspergualin, mizoribine, mycophenolate 2-morphorinoethyl, cyclosporin, rapamycin, tacrolimus monohydrate, leflunomide, and OKT-3.

Other objects, advantages and applications of this invention will be made apparent by the following detailed description. The description makes reference to preferred and illustrative embodiments of the invention presented in the accompanying drawings.

DETAILED DESCRIPTION OF PREFERRED EMBODIMENTS

Figure 1A:
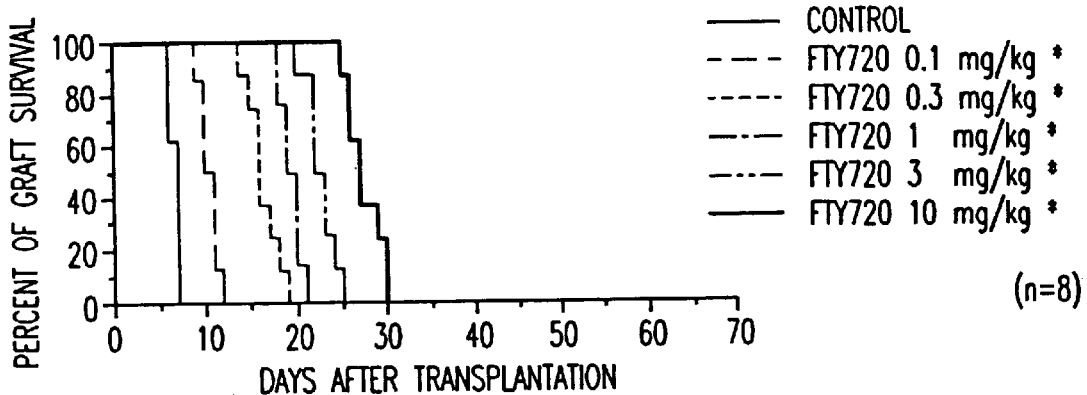
FIG. 1 the effects of FTY720, CsA, and TRL on skin graft survival in the MHC-incompatible rat strain system. Each curve on the graph represents an experiment using one of the three compounds. The vertical axis (0–100) depicts the percent survival of the grafted tissue. The horizontal axis depicts the number of days after transplantation. Each of the lines represents various dosages used, as indicated at the right. [* indicates p<0.05, generalized Wilcoxon test with Hommel s multiple comparison test vs. control]

Lymphocyte homing involves the physiological process of lymphocytes seeking out and localizing to specific tissues and micro-environments in an animal (39). Generally, cell adhesion and binding to cell-surface receptors control how lymphocytes home to specific tissues or recirculate through blood or lymph. Certain lymphocyte homing receptors, including CD62L, CD49d/$\beta$7 integrin, CD11a/CD18, and their ligands (GlyCAM-1, MAdCAM-1, ICAM-1, etc.) are expressed on the cell surface of high endothelial venules (HEV), the small blood vessels of the lymph nodes. CD62L (L-selectin) (30) and CD49d/$\beta$7 integrin ($\alpha_4\beta_7$ integrin) (31) bind GlyCAM-1 (32) and MAdCAM-1 (33), respectively, and both are expressed on cell surface of HEV in lymph nodes and Peyer's patches (lymphoid tissues of the intestine). The presence of these and other receptors and ligands on cells of an animal and on the lymphocytes forms the basis of the lymphocyte homing process.

Conducting the initial targeting of naive lymphocytes as well as the continuous distribution of other lymphocytes, the lymphocyte homing process plays a key role in immune system development and surveillance. Physiological evidence indicates that most subsets of mature lymphocytes are in continuous recirculating motion through blood or lymph vessels and the tissues of an animal. In addition, some lymphocyte subsets show a strong tissue specificity. For example, memory and effector lymphocytes, in particular, home in on inflamed skin or intestinal lamina.

Clearly, the ability to affect lymphocyte homing can be directly tied to methods for suppressing the immune system. For example, a composition that causes lymphocytes to home in the intestinal lamina will result in fewer lymphocytes available to react at another tissue within an animal. Since it is the lymphocytes and immune cells that control the immune response, dictating lymphocyte activity effects the scope and strength of their response. Furthermore, since directing lymphocytes to specific regions or tissues does not present detrimental physiological consequences, no toxic side effects to the immune cells would result by affecting lymphocyte homing, creating a safer immunosuppression therapy.

While some research discusses methods for manipulating lymphocyte homing, for example with the use of cell surface receptors and genetic modification, chemical compounds that interact with the lymphocyte homing process have not been widely used or discussed. The identification of the important characteristics of the ALH-immunosuppressive compositions and their uses, as described in this invention, opens a new avenue into immunosuppression treatments and therapies. Furthermore, one skilled in the art will appreciate that the invention can be used in methods and assays to identify the molecular interactions of the intestinal immune system, the migration of the involved cells (43), and the importance of these processes to normal and disease states.

In many cases, these compositions can be administered orally. The examples below detail the use of FTY720 by oral administration. One skilled in the art is familiar with numerous methods and tests for determining the effectiveness of a selected route of administration. Furthermore, pharmaceutically or physiologically acceptable carriers or excipients for use with the 2-aminopropane-1,3-diol compounds or benzene compounds noted herein are known in the art or can be readily found by methods and tests known in the art. And, pharmaceutically and physiologically acceptable salts of these compounds can also be determined and used by one skilled in the art.

In the examples that follow, FTY720, a 2-aminopropane-1,3-diol compound, dose-dependently prevented acute rejection in allograft models. The combination treatment of FTY720 with CsA or TRL showed a synergistic effect on prevention of acute rejections but did not enhance toxic side effects of the drugs CsA or TRL. Unlike CsA or TRL, FTY720 does not inhibit the expression of IL-2 mRNA or the production of IL-2 in alloantigen stimulated T cells. FTY720 remarkably decreased the number of circulating lymphocytes, especially T cells, in peripheral blood of rats, dogs and monkeys. Furthermore, FTY720 caused an atrophy in the T cell region of spleen in vivo.

In addition, lymphocyte homing to lymph nodes and Peyer's patches was accelerated by FTY720. The FTY720 activity sequesters immunologically competent T cells to high endothelial venules (HEV) in lymph nodes and Peyer's patches. Thus, FTY720 possesses a unique mechanism of action, distinct from other immunosuppressants such as CsA or TRL. Based on these results, administration of ALH-immunosuppressive compositions prevents acute rejection without producing the side effects of individual drugs known in human organ transplantations. A number of other immunosuppressant compounds can also be combined with the 2aminopropane-1,3-diol compounds or benzene compounds to enhance immunosuppressive effects of the ALH-immunosuppressive composition, including, but not limited to: steroid(s) (prednisolone, methylprednisolone, dexamethasone, hydrocortisone and the like) (13-14); non-steroidal anti-inflammatory agent(s); azathioprine (13); mizoribine (14); brequinar sodium; deoxyspergualin; mycophenolate 2-morphorinoethyl; mycophenolate derivatives; cyclosporin; cyclosporin derivatives; rapamycin; tacrolimus monohydrate; leflunomide; OKT-3 (48); or various other immunosuppressive antibodies and compounds discussed herein or known in the art. Methods such as those described in these examples, and examples 5–9 in particular, can be incorporated into assays for detecting the presence or absence of ALH-immunosuppressive compounds. In this way, methods to screen numerous samples believed to contain ALH-immunosuppressive activity can identify chemical or biological compounds with detectable levels of ALH-immunosuppressive activity. For example, a sample can be administered to an animal, at various selected doses, and the animal's lymphoid tissues and blood assayed for the number or amount of lymphocytes present.

The use of prelabeled lymphocytes can also be incorporated into these methods. The sample believed to contain ALH-immunosuppressive activity is first administered and then the prelabeled lymphocytes are transfused. Certain patterns of prelabeled lymphocyte populations in lymphoid tissues, other tissues, or blood will indicate accelerated lymphocyte homing activity. FIG. 13 represents typical results that may be obtained. In the example of FIG. 13, the use of male lymphocytes transfused into female recipients constitutes the use of prelabeled lymphocytes. The male, prelabeled lymphocytes are detectably different from the recipient animal's lymphocytes, in this case, the label being at the genetic level. Accordingly, prelabeled lymphocytes, as used in this invention, are not limited to a specific chemical or other label bound, associated with, or otherwise operably attached to a lymphocyte.

FIG. 13 indicates accelerated lymphocyte homing to peripheral lymph nodes, Peyer's patch, and mesenteric lymph nodes, evidenced by the increased numbers of cells present following administration of FTY720. Spleen, however, shows a reduction in the number of pre-labeled lymphocytes when treated with FTY720. Thus, FTY720 possesses ALH-immunosuppressive activity. In addition, the ALH-immunosuppressive compositions may also be used in methods to reduce spleen lymphocyte levels.

The description and examples below specifically employ the FTY720 compound and combinations with CsA and TRL in the ALH-immunosuppressive compositions. The inclusion of these examples should not be taken to limit the scope of the invention. Many other compounds can be substituted for those exemplified, as discussed throughout this disclosure. One skilled in the art will appreciate that modifications to the compounds selected for use, the combinations of compounds used, and the dosages used, for example, can be made to arrive at physiologically acceptable alternatives within the scope of this invention.

EXAMPLE 1

Effect of FTY720 on rat skin allograft survival in major histocompatibility complex (MHC)-incompatible system.

A rat skin allograft survival assay employing MHC-incompatible rat strains as donor and acceptor has been described (Reference 21, specifically incorporated herein by reference). Two MHC-incompatible rat strains were selected, WKAH donor ($RT1^k$) and F344 recipients ($RT1^{lv1}$). Full-thickness skin grafts (2.0×2.0 cm square) were transplanted to the lateral thorax of recipients and wrapped with sterile, bactericidal gauze. The chest was then wrapped with an elastic bandage. Five days after transplantation, the wraps were removed and the grafts inspected daily for rejection. Rejection was defined as more than 90% necrosis of graft epithelium.

Figure 1B:
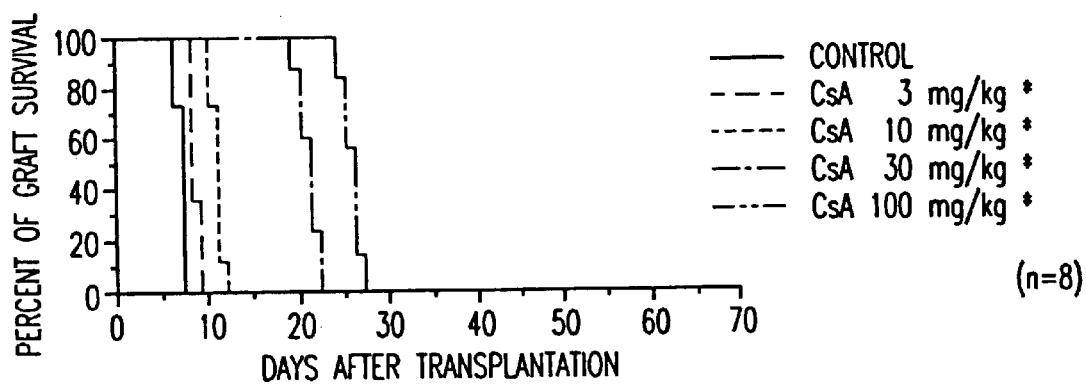
Figure 1C:
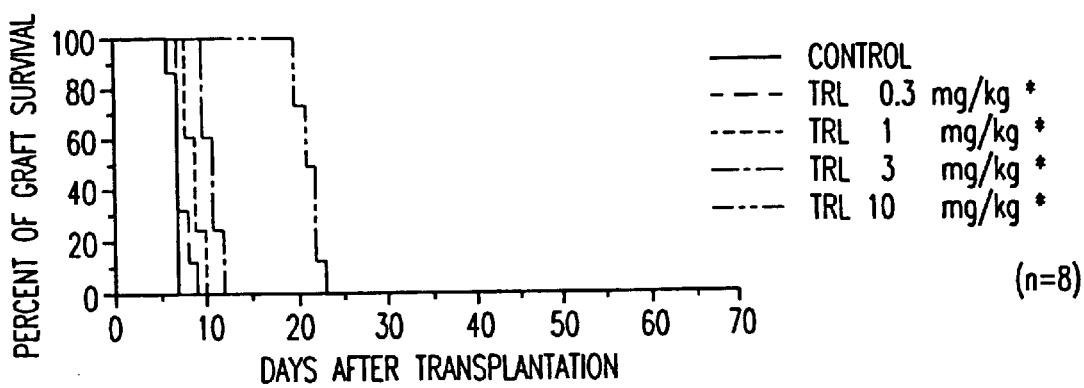

All skin grafts in control (vehicle-treated) groups were rejected in 6 to 7 days after the transplantation. FTY720 significantly prolonged graft survival at an oral dose of 0.1 mg/kg or more in a dose-dependent manner (FIG. 1). Administration with FTY720 at an oral dose of 10 mg/kg for 14 days resulted in a prolongation of graft survival with median survival time (MST) of 27.0 days without renal toxicity or other toxic signs. As shown in FIG. 1, both CsA and TRL were also effective at oral doses of 3 mg/kg or more and 0.3 mg/kg or more, respectively, in this model. Fourteen days repeated administration of CsA at 100 mg/kg or TRL at 10 mg/kg resulted in prolonging graft survival with MST of 26.0 days or 22.5 days, respectively. However, one of eight recipients died within the course of administration of CsA at 100 mg/kg. These findings indicate that FTY720 prolongs the skin allograft survival across a MHC barrier and is more potent than either CsA or TRL.

Figure 2A:
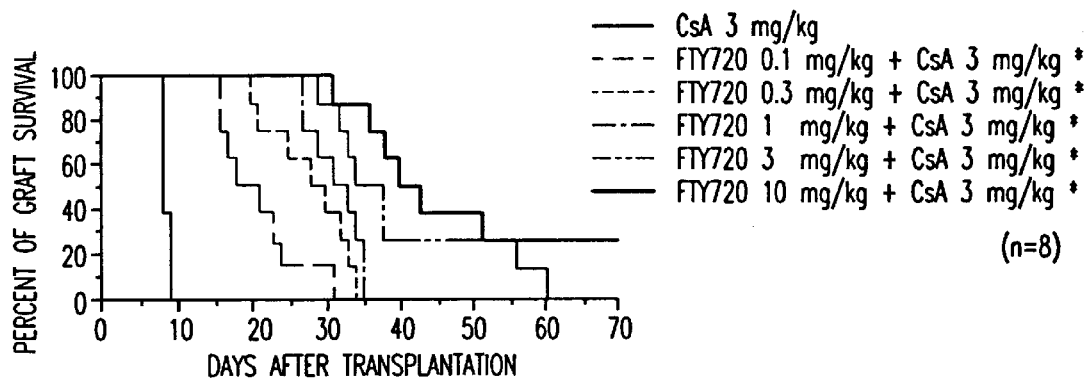
FIG. 2 the effects of FTY720 in combination with CsA or TRL on skin allograft survival in the MHC-incompatible rat strain system. Each curve on the graph represents an experiment using a combination of FTY720 with CsA or TRL. The combination used and the dosage are indicated by the lines at right. Figure results appear as in the format of FIG. 1. [* indicates p<0.05, generalized Wilcoxon test with Hommel s multiple comparison test vs. CsA alone or TRL alone]
Figure 2B:
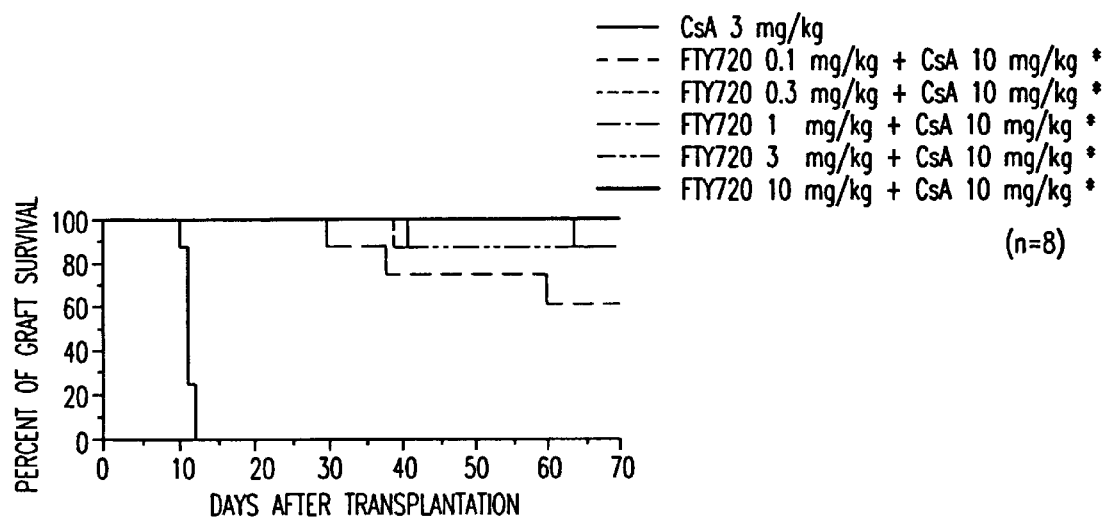
Figure 2C:
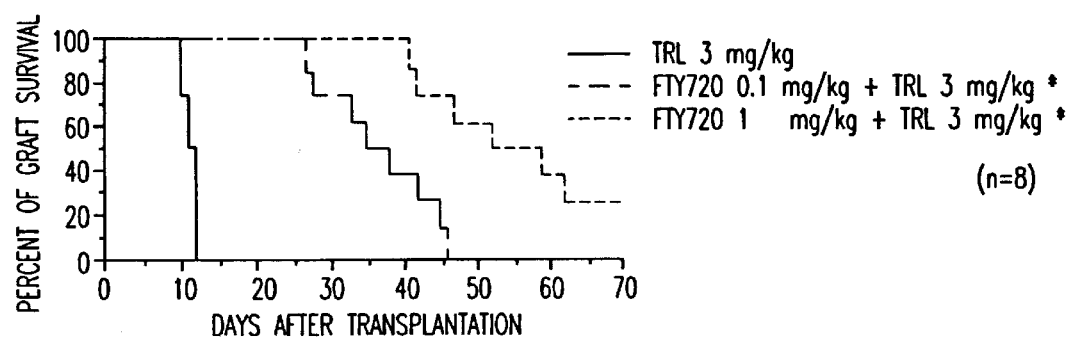

In clinical organ transplantations, combination therapies of CsA with prednisolone or other immunosuppressants are widely used to reduce the side effects of the individual drugs (13-14). To demonstrate that the use of FTY720 in combinations with CsA produces advantageously synergistic effects, experimental allograft models were used. One examined FTY720 combined with CsA at a dose of 3 or 10 mg/kg in the MHC-incompatible rat skin allograft model. Comparing the effects of the therapy with either of FTY720 or CsA alone (FIG. 1), the combined administration of FTY720 with CsA at 3 mg/kg or 10 mg/kg brought a significant prolongation of skin allograft survival (FIG. 2). In combination with CsA at 10 mg/kg, FTY720 even at a dose of 0.1 mg/kg remarkably prolonged the allograft survival, with an MST of more than 70 days in five out of eight recipient rats (FIG. 2). The values of combination index, which were calculated by the method of Kahan et al. (22), were less than 0.1 by combined administration of FTY720 with CsA, indicating a synergistic effect.

The results of these initial combination therapy experiments show that FTY720 acts synergistically with CsA. A similar synergistic effect was obtained in combination therapies of FTY720 and TRL in this model (FIG. 2). In MHC-compatible rat strains of LEW donor and F344 recipient (21), FTY720 at 0.03 mg/kg or more also prolonged the survival of skin allograft significantly and showed a synergistic effect on prolonging allograft survival in combination with CsA at 3 mg/kg (data not shown).

EXAMPLE 2

Effects of FTY720 on heterotopic cardiac allograft survival in MHC-incompatible rat strain system.

The effect of FTY720 on heterotopic cardiac allograft survival was compared with those of CsA and TRL by using WKAH donor (RT1k) and ACI recipient (RT1$^{av1}$) rats. This procedure is detailed in reference 23, specifically incorporated herein by reference. Hearts from donors were implanted in the cervical portion of recipients by the technique of Miller et al. (40). The pulmonary artery of the donor heart was anastomosed to the right external jugular vein of the recipient in an end-to-side manner. The donor's brachiocephalic artery was anastomosed to the left common carotid artery of the recipient in an end-to-end manner. The day of grafting was day 0 and cardiac arrest was defined as the last day of graft survival. A graft heart surviving over 100 days was considered an indefinite or long-term survivor.

Figure 3A:
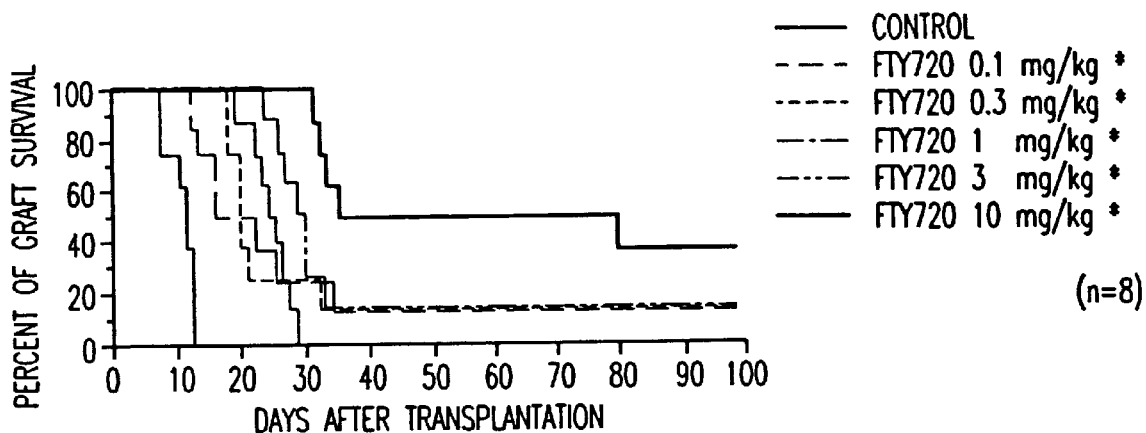
FIG. 3 effects of FTY720, CsA, and TRL on heterotopic cardiac allograft survival in the MHC-incompatible rat strain system. Each curve on the graph represents an experiment using one of the three compounds. The compound used and the dosage are indicated by the lines at right. Figure results appear as in the format of FIG. 1. [* indicates p<0.05, generalized Wilcoxon test with Hommel s multiple comparison test vs. control]
Figure 3B:
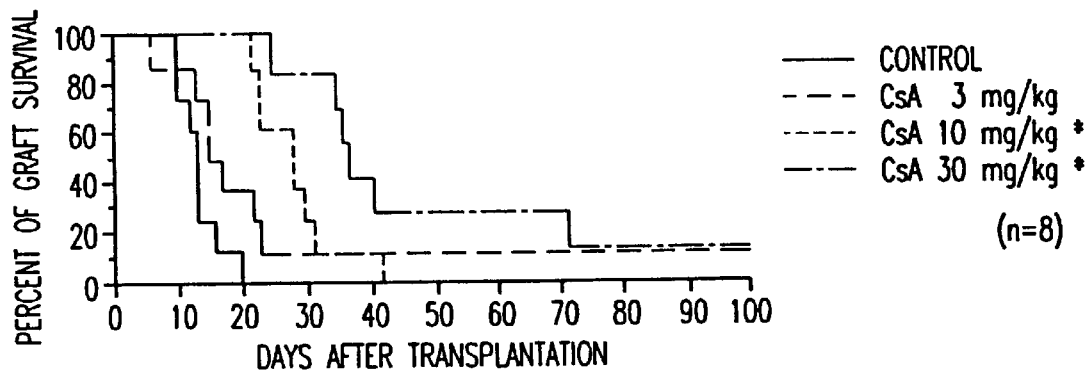
Figure 3C:
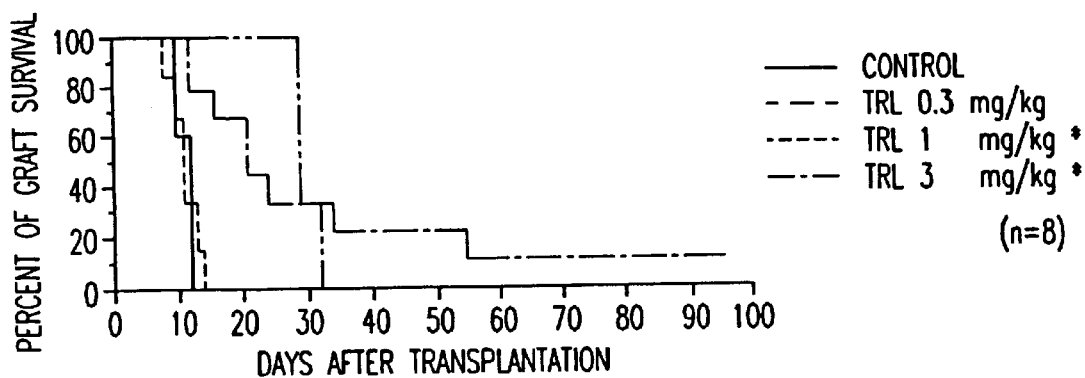

The results are illustrated in FIG. 3. All cardiac allografts in control (vehicle-treated) group were rejected within 14 days (MST:12.0 days) after the transplantation. Treatment with FTY720 at an oral dose of 0.1 mg/kg or more significantly prolonged the cardiac allograft survival. The MST of FTY720 administration with 0.1, 0.3,1, 3 and 10 mg/kg for 14 days were 20.0, 21.0, 25.5, 29.5 and 58.5 days, respectively (FIG. 3). FTY720 at 10 mg/kg induced a long-term or indefinite graft survival of more than 100 days in three out of eight recipient rats. CsA (at doses of 10 mg/kg or more) and TRL (at doses of 1 mg/kg or more) significantly prolonged the cardiac allograft survival compared to control. However, these drugs hardly induced long-term graft survival even at the highest dose tested (FIG. 3). These results show that FTY720 is more potent than CsA or TRL in rat cardiac allograft and that this compound has the capability to induce indefinite graft acceptance in vascularized organ transplantations.

Figure 4A:
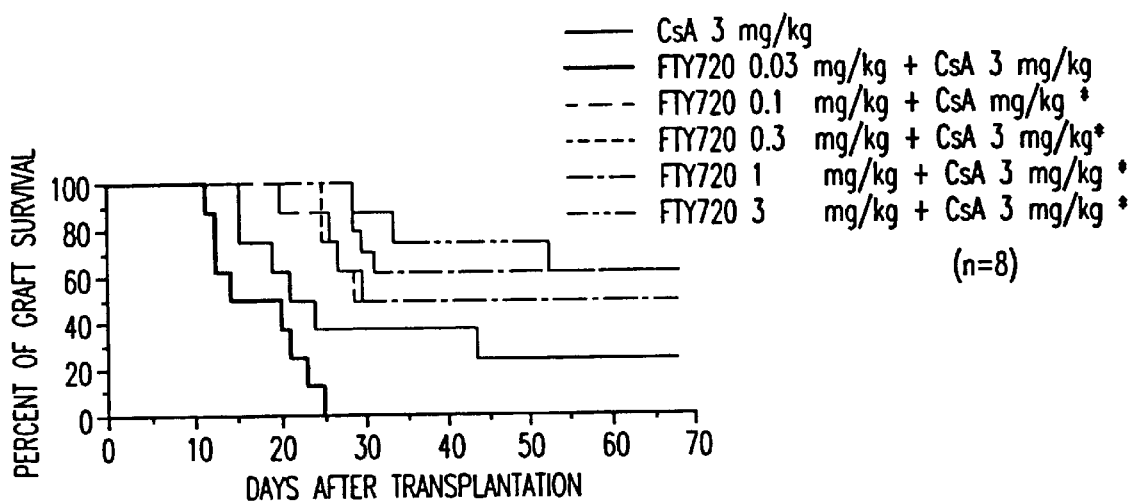
FIG. 4 effects of FTY720 in combination with CsA or TRL on heterotopic cardiac allograft survival in the MHC-incompatible rat strain system. The combination used and the dosage are indicated by the lines at right. Figure results appear as in the format of FIG. 1. [* indicates p<0.05, generalized Wilcoxon test with Hommel s multiple comparison test vs. CsA alone or TRL alone]
Figure 4B:
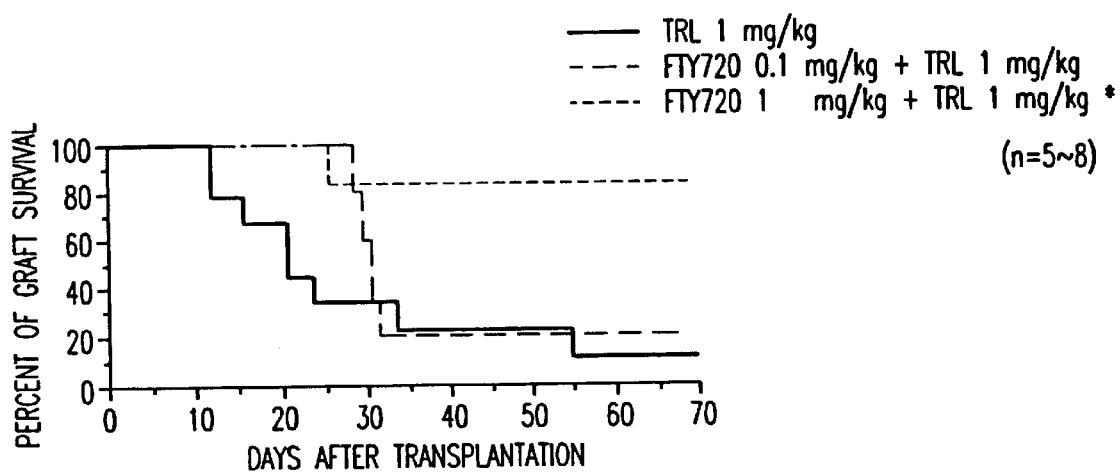
Figure 5A:
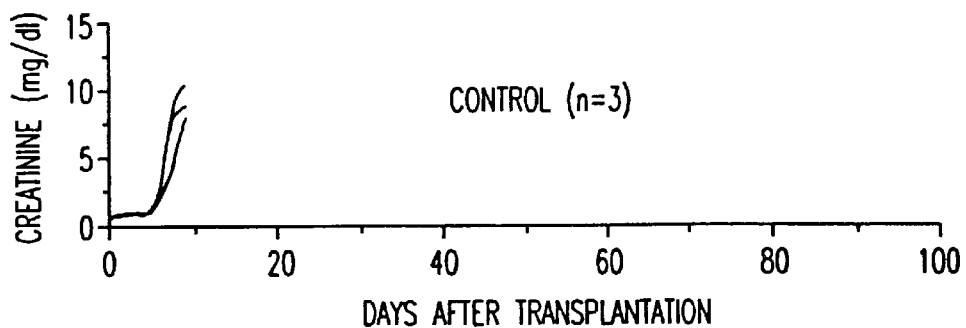
FIG. 5 serum creatine levels in beagle recipients with mongrel kidney allografts. Serum creatine levels, represented in the vertical axis as mg/dl, were determined at various days after transplantation, represented by the horizontal axis. Each line depicts the results from an individual animal.
Figure 5B:
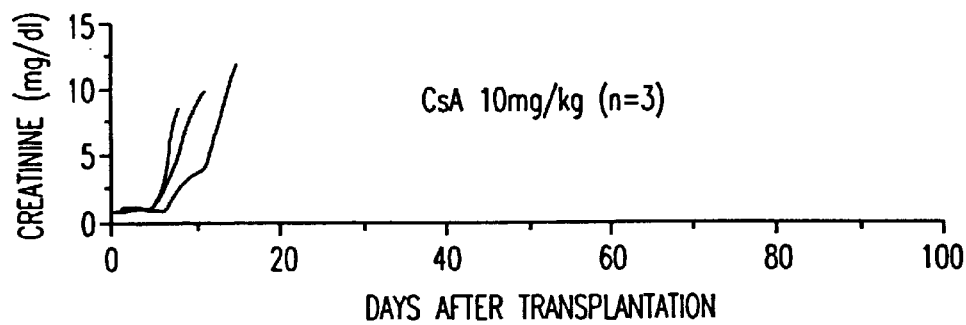
Figure 5C:
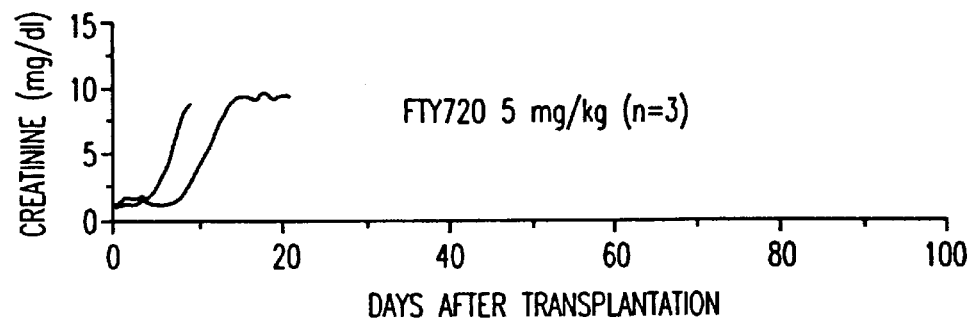
Figure 5D:
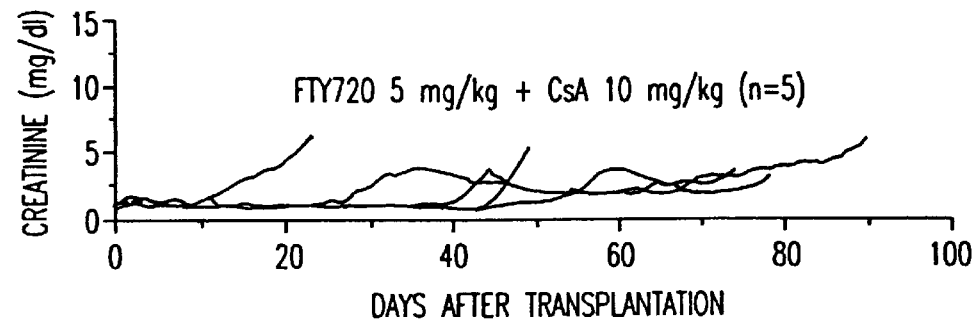

The effect of FTY720 in combination with CsA was examined in this cardiac allograft model, using WKAH donors and ACI recipients. FTY720 at an oral dose of 0.1 mg/kg or more significantly prolonged the allograft survival in combination with CsA at 3 mg/kg as compared with the treatment of either FTY720 or CsA alone (FIG. 4). FTY720, when concomitantly administered with CsA, produced indefinite graft survival in more than 50% of recipients. FTY720 at an oral dose of 1 mg/kg combined with TRL at a dose of 1 mg/kg also showed a synergistic effect on graft survival in this model (FIG. 4). From these results, treatments of FTY720 concomitantly administered with CsA or TRL synergistically prolongs the graft survival and induces indefinite allograft acceptance more frequently than FTY720 alone.

EXAMPLE 3

Effect of FTY720 on canine renal allograft survival in combination with CsA.

Figure 6:
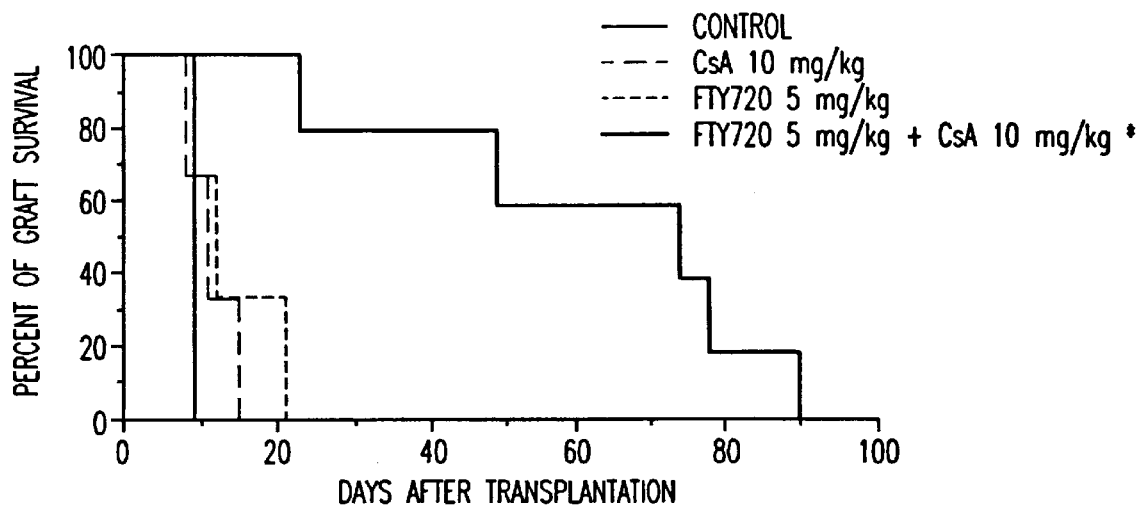
FIG. 6 effect of FTY720 and CsA, alone and in combination, on renal allograft survival in canines; mongrel donor and beagle recipient. Each graph represents an experiment using FTY720, CsA, or a combination of the two. The compound or combination used and the dosage are indicated at right. Figure results appear as in the format of FIG. 1. [* indicates p<0.05, generalized Wilcoxon test with Hommel s multiple comparison test vs. control]
Figure 7:
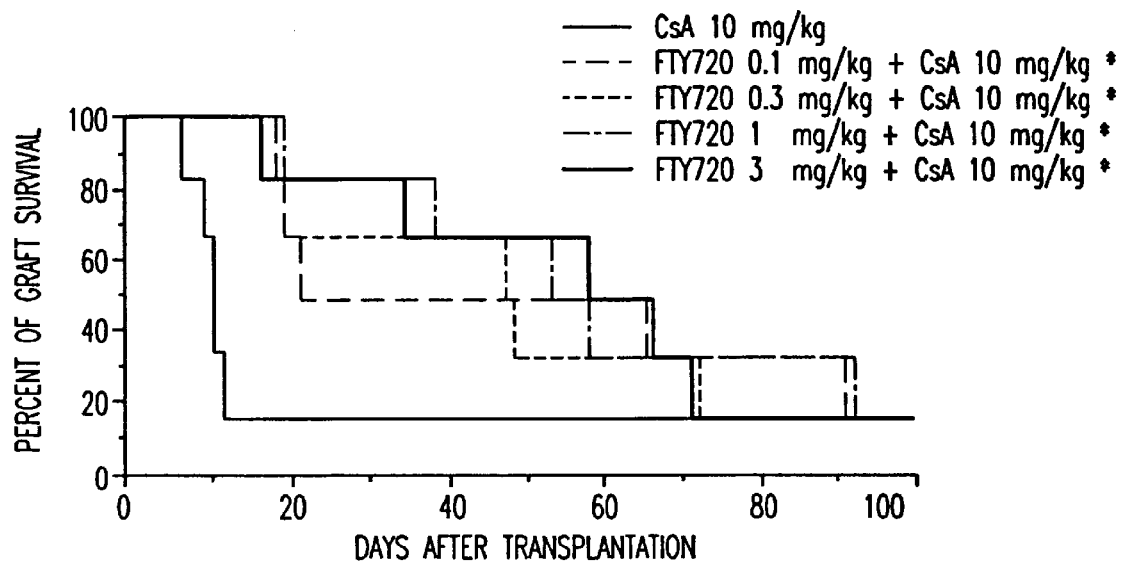
FIG. 7 effect of FTY720 combined with CsA on graft survival in canines; mongrel renal allograft donor and beagle recipient. The combination used and dosage are given at right, corresponding to each curve of the results found in the graph. CsA alone is included for comparison. Figure results appear as in the format of FIG. 1. [* indicates p<0.05, generalized Wilcoxon test with Hommel s multiple comparison test vs. CsA 10 mg/kg treated group]

In a canine renal allograft model, either azathioprine or mizoribine in combination with CsA was reported to show a significant prolongation of the graft survival as compared with each drug alone (27-28). The effect of FTY720 in combination with CsA on renal allograft survival was investigated by using mongrel donors and beagle recipients in dogs (24–26, specifically incorporated herein by reference). Kidneys from mongrel donor dogs were transplanted into beagle dogs in the right iliac fossa, and the recipient dogs were then nephrectomized bilaterally. Levels of serum creatine and blood urea nitrogen were measured to monitor survival. Graft rejection was defined as the day when either serum creatine levels increased to more than 10.0 mg/dL or blood urea nitrogen levels elevated to more than 200 mg/dL. As shown in FIG. 5, in control (vehicle-treated) group, levels of serum creatinine irreversibly elevated within 10 days, and all animals died within 17 days due to renal dysfunction by acute rejection. The levels of serum creatinine also elevated within 14 days in 5 mg/kg FTY720 or 10 mg/kg CsA-treated group. In combinations of FTY720 and CsA, the serum creatinine levels in four out of five recipients were completely maintained at normal levels for at least 30 days after the transplantation (FIG. 5). The survival curves are illustrated in FIG. 6. MST in the control allograft group was 9.0 days. Treatment of FTY720 at 5 mg/kg or CsA at 10 mg/kg resulted in slightly prolonging, not significantly, graft survival (MST: FTY720-treated group: 12.0 days, CsA-treated group: 11.0 days). However, combination treatments of FTY720 at 5 mg/kg with CsA at 10 mg/kg resulted in significantly prolonging graft survival with MST of 74.0 days. FTY720 at lower doses (0.1 to 3 mg/kg) also prolonged renal allograft survival significantly in combination with CsA at 10 mg/kg (FIG. 7), and there was no severe toxic signs in the kidney and liver functions. With the combination treatment of FTY720 with CsA, the blood concentration of creatine was unchanged. These results suggests that FTY720 acts synergistically with CsA.

EXAMPLE 4
Effect of FTY720 on graft versus host reaction (GvHR) in rats.

Figure 8:
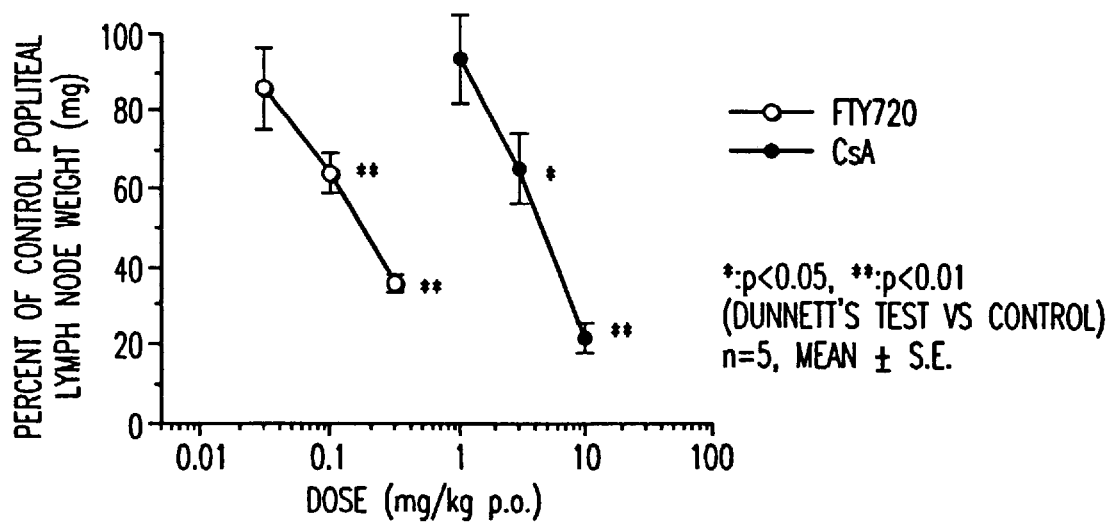
FIG. 8 effect of FTY720 and CsA on enlargement of popliteal lymph node caused by GvHR in rats. The results depict the size of popliteal lymph node (as a percent of control popliteal lymph node weight; vertical axis) from various dosages of either FTY720 or CsA (horizontal axis). Open circle represent FTY720-treated animals and filled circles represent GsA-treated animals.

Spleen cells ($2.5 \times 10^6$ cells) from LEW rats were injected subcutaneously into the footpad of (LEW×BN) F1 ($RT1^{l/n}$) rats, inducing enlargement of draining and the weight of popliteal lymph node (29). Weight increased to the maximum after 7 days. FTY720 and CsA, administered orally, significantly inhibited the enlargement in popliteal lymph node at doses of 0.1 mg/kg or more and of 3 mg/kg or more, respectively, in a dose-dependent manner (FIG. 8). Thus, the immunosuppressive activity of FTY720 was 30-fold more potent than that of CsA in local GvHR in rats.

Figure 9:
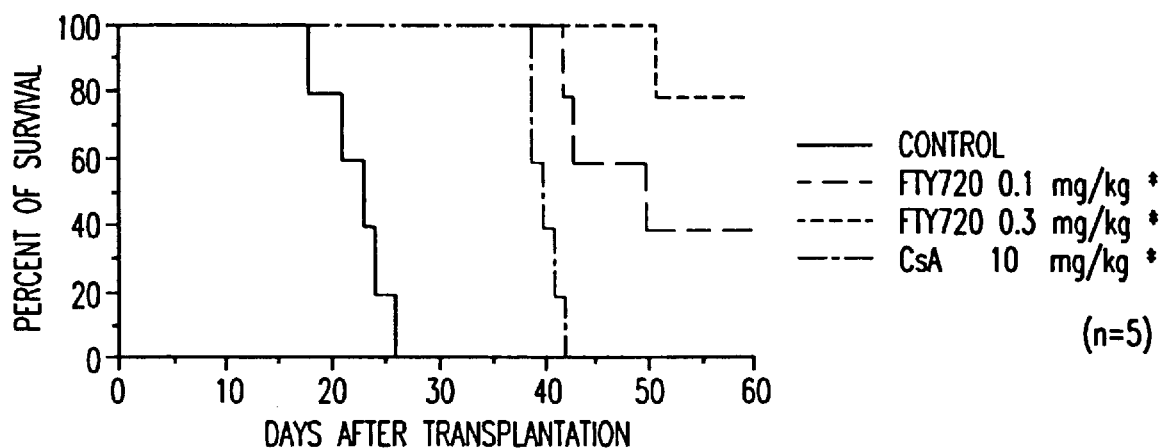
FIG. 9 effect of FTY720 and CsA on lethal GVHR in rats. Each curve on the graph represents an experiment using one of the compounds, or control. The compound used and the dosage are indicated by the lines at right. Figure results appear as in the format of FIG. 1. [* indicates p<0.05, generalized Wilcoxon test with Hommel s multiple comparison test vs. control]

To examine the effect of FTY720 in preventing the lethal GvHR, splenic lymphocytes from LEW donor rats ($1 \times 10^8$ spleen cells) were injected intravenously into cyclophosphamide-pretreated (LEW×BN)$F_1$ recipients. Cyclophosphamide (Shionogi Co. Ltd; Osaka, Japan) was given at a 200 mg/kg dose. The results are shown in FIG. 9. In control (vehicle-treated) group, all rats developed severe GvHR-associated symptoms, including redness of skin and hair loss, within 15 days after the injection of LEW spleen cells and died with MST of 22.0 days. CsA at a dose of 10 mg/kg for 30 days significantly prolonged the survival of the recipient rats. However, cessation of CsA administration caused the severe symptoms of GvHR and, subsequently, all of recipients died within 42 days (MST: 40.0 days). Oral administration of FTY720 at a dose of 0.1 mg/kg for 30 days prevented the development of GvHR-associated symptoms and prolonged the host survival significantly (MST: 50.0 days). Treatment with FTY720 at a dose of 0.3 mg/kg induced survival of more than 60 days in four out of five rats without the GvHR-associated symptoms. FTY720 induced long-lasting unresponsiveness by treatment with low doses (0.1 to 0.3 mg/kg) in the lethal GvHR model, indicating complete prevention of GvHR.

EXAMPLE 5
Effect of FTY720 on IL-2 mRNA expression in alloantigen-stimulated splenic T cells in rats.

CsA and TRL were reported to inhibit IL-2 production and IL-2 mRNA expression in antigen or mitogen-stimulated helper T cells (9,11). The effect of FTY720 on alloantigen-induced IL-2 mRNA expression was examined as compared to those of CsA and TRL in allogeneic mixed lymphocyte cultures using splenic T nLn cells of F344 rats as responder cells and mitomycin C-pretreated WKAH rat spleen cells as stimulator cells (21). Each of the compounds FTY720, CsA, and TRL were added to cultures (F344 rat spleen cells at $5 \times 10^6$ cells/mL in RPMI 1640 medium containing and 10% fetal calf serum) to the indicated concentration. The housekeeping gene HPRT was used as an internal control in order to compare levels of IL-2 mRNA levels relative to the HPRT mRNA levels, as detailed below.

Allogeneic mixed lymphocyte culture was carried out by using nylonnonadherent spleen cells of F344 rat ($RT1^{1v1}$) as responder cells and the spleen cells of WKAH rat ($RT1^k$) pretreated with 40 µg/ml of mitomycin C for 30 min as stimulator cells. In the presence of various concentrations of FTY720, CsA, and FK506, the responder cells ($5 \times 10^5$ cells/well) were cultured with an equal number of stimulator cells in 2 ml of RPMI 1640 medium containing 10% fetal calf serum at 37° C. in 5% $CO_2$. After culturing for 48 hours, the cells were recovered by centrifugation. The expression of IL-2 mRNA in the cells was determined by a polymerase chain reaction (PCR) method.

Total RNA was reverse transcribed in 60 ml of buffer solution containing 10 mmol/L Tris-HCl (pH 8.3),50 mM KCl, 5 mM $MgCl_2$, 1 mM each dNTP (dATP, dGTP, dTTP and dCTP), 60 U RNase inhibitor (Takara Ltd. Tokyo, Japan), 15 U avian myelobalastosis virus reverse transcriptase (Takara Ltd.) and 150 pmol random 9mers at 30° C. for 10 min and 42° C. for 30 min. Primer sequences for IL-2 and hypoxanthine-guanine phosphoribosyltransferase (HPRT) were taken from the previous report (44).

The length in base pairs of the PCR products of IL-2 and HPRT are 351 and 608 bp respectively. A cDNA equivalent of 100 ng total RNA was amplified in a 25 ml volume containing 10 mM Tris-HCl (pH 8.3), 50 mM KCl, 2 mM $MgCl_2$, 200 mM each dNTP (dATP, dGTP, dTTP and dCTP), 200 nM appropriate primer pair and 0.625 U Taq DNA polymerase (Takara Ltd.). After an initial denaturation step, the cDNA mixture was subjected to 30 (IL-2), or 24 (HPRT), amplification cycles, each cycle consisting of denaturation at 94° C. for 15 sec, annealing at 72° C. (IL-2) or 65° C. (HPRT) for 15 sec, and extension at 72° C. for 15 sec with an automatic thermocycler GENE AMP PCR SYSTEM 9600, Perkin Elmer Cetus). An aliquot (10µl) of the PCR product was electrophoresed on 2% agarose gel, and amplified DNA-fragments were stained with SYBR Green I (Molecular Probes). Fluorescence intensity of the specific bands was visualized by fluorescence image analyzer FLUOR IMAGER 575, Molecular Dynamics).

Figure 10:
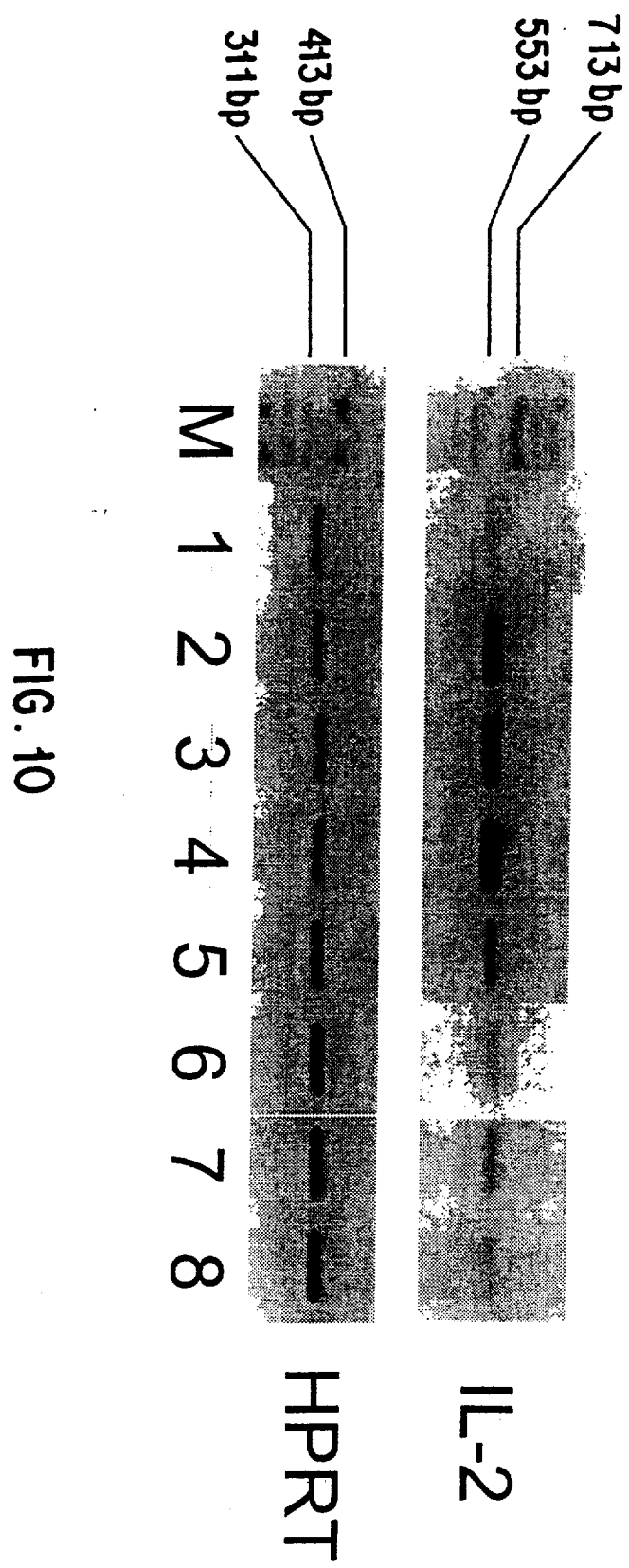
FIG. 10 effect of FTY720, CsA, and TRL on IL-2 mRNA levels in alloantigen-stimulated splenic T cells in rats. Lane M is molecular weight markers (size indicated by numbers of base pairs at left); lane 1 is unstimulated T cells; lane 2 is alloantigen-stimulated T cells; lane 3 is FTY720 treated at 100 nM; lane 4 is FTY720 treated at 1000 nM; lane 5 is CsA treated at 10 nM; lane 6 is CsA treated at 100 nM; lane 7 is TRL treated at 0.1 nM; and lane 8 is TRL treated at 1 nM. The levels of IL-2 mRNA can be determined from the band marked "IL-2" and compared with the control, housekeeping gene HPRT (hypoxanthine-guanine phosphoribosyltransferase) mRNA levels as known in the art.

CsA at 10 nM or more and TRL at 1 nM or more inhibited the IL-2 mRNA expression down to levels approaching the unstimulated, control level. On the other hand, FTY720 did not inhibit the IL-2 mRNA expression even at the concentration of 1000 nM. (FIG. 10). In the same concentration range, FTY720 did not inhibit the production of IL-2 by alloantigen- or concanavalin A-stimulated lymphocytes in rats (21). These results show that FTY720 suppresses the immune response to alloantigen by a mechanism other than inhibiting IL-2 production from helper T cells. FTY720, in combination with CsA or TRL, shows a synergistic effect on allograft survival because of its distinct mechanism of action from CsA or TRL.

Numerous other methods for detecting the effect of ALH-immunosuppressive compositions, or the presence of ALH-immunosuppressive activity in a sample, exist. For example, measuring the expression of cytokines, such as IL-2, using the polymerase chain reaction or RT-PCR to detect mRNA levels is a straightforward and powerful method (41-42).

EXAMPLE 6
Effect of FTY720 on lymphocyte homing in rats.

The lymphocyte contents of peripheral blood and spleen in FTY720-treated intact or allografted rats were analyzed by two color flow cytometry using anti-rat CD3 and anti-rat CD45RA or A/B monoclonal antibodies (21). Lymphocytes were stained with FITC-conjugated anti-CD3 (clone: 1F4, Caltag Laboratories, South San Fransisco, Calif.) (45) and phycoerythrin-conjugated anti-CD45RA or A/B (clone:OX-33, Pharmingen, La Jolla, Calif.) (46) monoclonal antibodies. The T cell and B cell contents were determined by two-color flow cytometry analysis using a flow cytometer (EPICS-XL; Coulter Co.).

Figure 11:
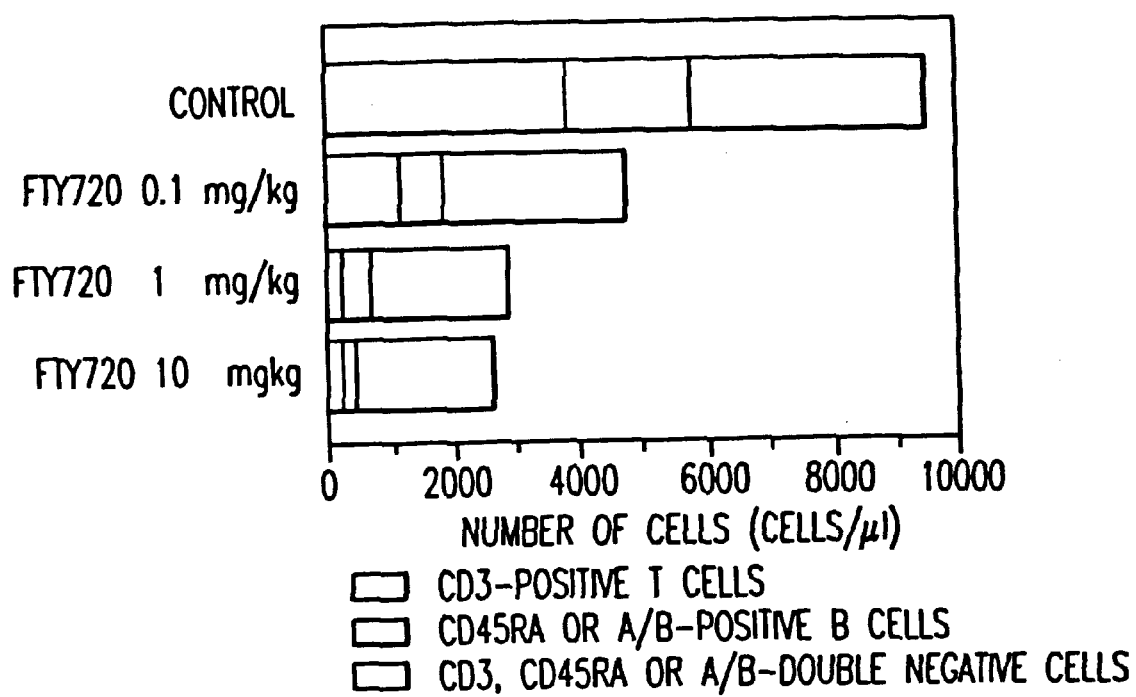
FIG. 11 white blood cell contents in peripheral blood of LEW rats administered FTY720. The type of lymphocyte is indicated by the shaded or open boxes, as shown at the bottom. The horizontal axis represents the number of cells (cell/$\mu$l). The vertical axis represents the dosage of FTY720 given the animals. Peripheral blood was collected 6 hours after the administration of FTY720. The results are the mean numbers from six animals.
Figure 12:
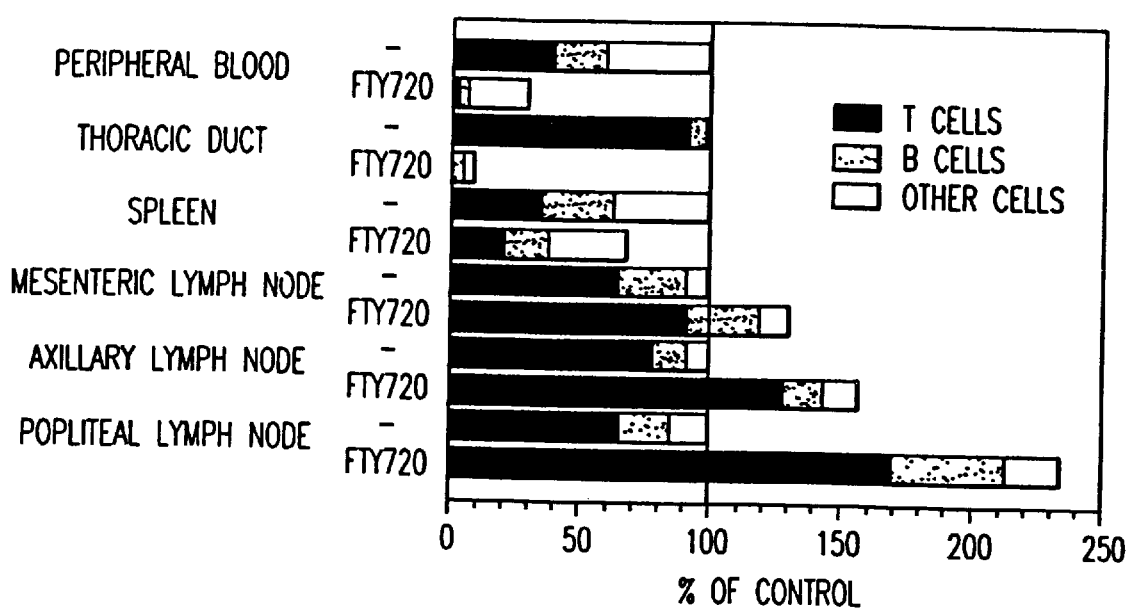
FIG. 12 effect of FTY720 on lymphocyte populations of various lymphoid tissues 6 hours after administration of FTY720 to rats (1 mg/kg oral). T cells, B cells, and other cells are represented by the shaded or open boxes, as shown at right. The horizontal axis represents the number of cells as a percent of the control level. The vertical axis represents each of the lymphoid tissues surveyed, with (FTY720) and without (-) FTY720 treatment. The results are the mean numbers from four to six animals.
Figure 13A:
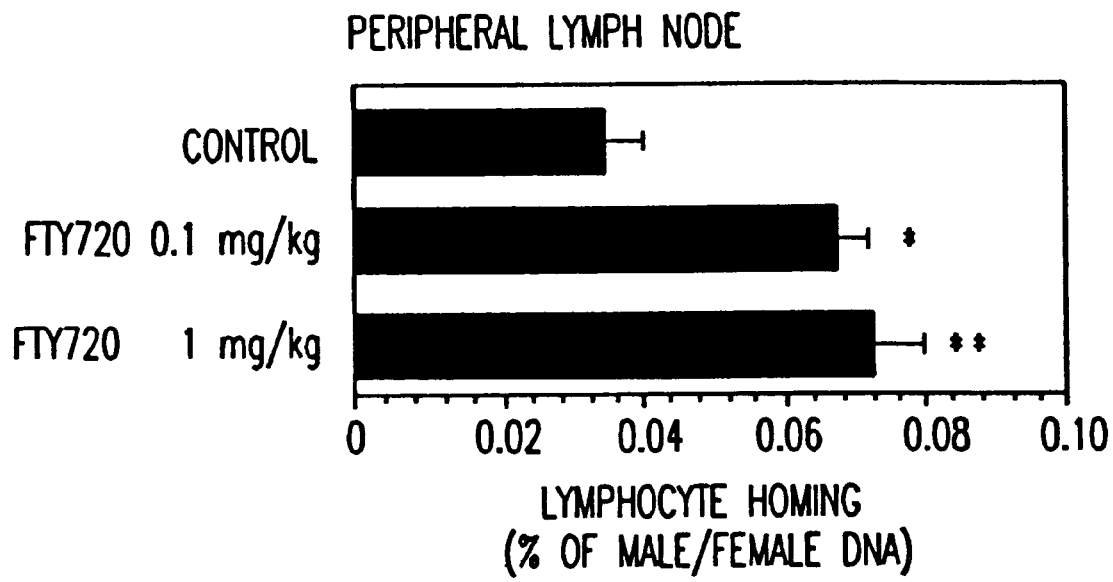
FIG. 13 effect of FTY720 treatment on lymphocyte homing to various lymphoid tissues in the rat. Each of the peripheral lymph node, Peyer's patch, mesenteric lymph node, and spleen lymphoid tissues was studied and graphs for each are depicted. The shaded boxes represent the number of transfused male F344 rat lymphocytes found in recipient female F344 rat lymphoid tissue (as a percent of the female cells present; horizontal axis) 30 minutes after the cells were intravenously injected. The cells were transfused 2.5 hours after administration of FTY720, at dosages noted in the vertical axis. Each experiment used four animals. [** indicates p<0.01 and * p<0.05 in Dunneft's test vs. control]
Figure 13B:
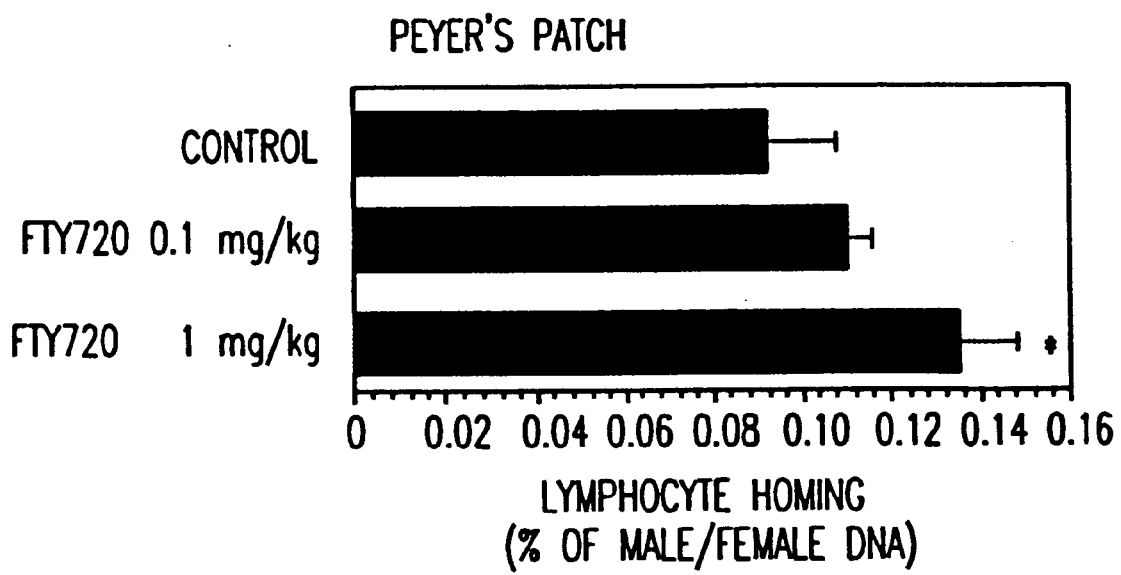
Figure 13C:
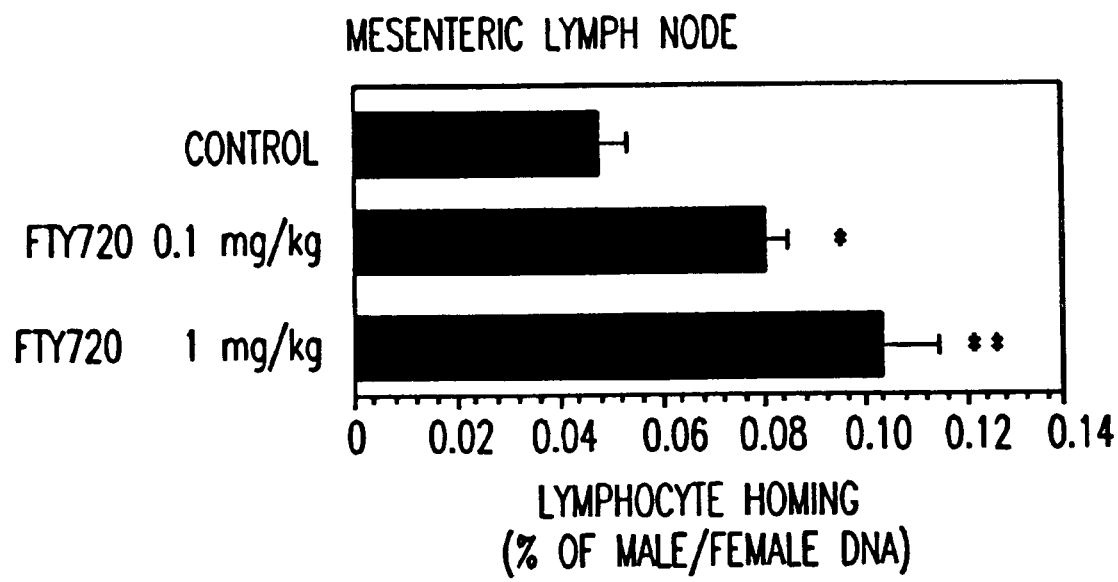
Figure 13D:
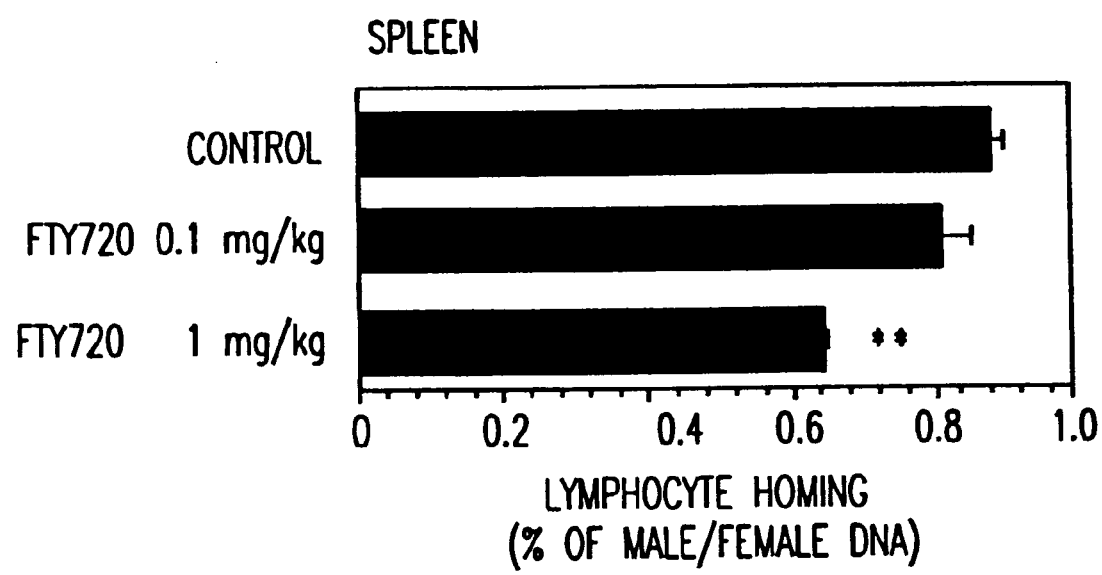

The numbers of CD3-positive T cells and CD45RA or A/B-positive B cells in peripheral blood were dramatically decreased within 6 hours after the oral administration with FTY720 at doses of 0.1 to 10 mg/kg (FIG. 11). In dogs and monkeys, as well as rats, oral administration with FTY720 also decreases the number of circulating lymphocytes in peripheral blood. The reduction of the number of T cells was especially remarkable. Withdrawal of FTY720 treatment recovered the number of lymphocytes in peripheral blood to the normal level within 2 weeks. FIG. 12 shows the cell numbers in various lymphoid tissues in rats orally administered FTY720 at 1 mg/kg. FTY720 also induced a decrease in the number of T cells and B cells in spleen, thoracic duct, as well as peripheral blood. On the contrary, the numbers of T cells and B cells in mesenteric and peripheral lymph nodes were significantly increased by administration with FTY720. FTY720 did not effect the number of bone marrow cells, thymocytes, and polymorphonuclear cells (data not shown).

The decrease in circulating lymphocytes by FTY720 is due to the acceleration of lymphocyte homing to mesenteric and peripheral lymph nodes and Peyer's patches (FIG. 13). For this experiment, after 2.5 h of administering FTY720 at 0.1 mg/kg or 1 mg/kg orally to female F344 rats, lymphocytes from male F344 rat were transfused intravenously into the rats. Thirty minutes after the transfusion, the peripheral blood, spleen, mesenteric lymph nodes, axillary lymph nodes, Peyer's patches, liver, and lung were removed. PCR amplification of SRY-1 gene, which is Y-chromosome specific, detected male lymphocytes in the tissue samples. The PCR primer sequences for SRY amplification were taken from a previous report (47). After an initial denaturation step, the cDNA mixture was subjected to 32 amplification cycles, each cycle consisting of denaturation at 94° C. for 1 min, annealing at 65° C. for 30 sec, and extension at 72° C. for 1 min, using an automatic thermocycler (Perkin Elmer Cetus, Gene Amp PCR System 9600).

An aliquot (10$\mu$l) of the PCR products was electrophoresed on 2.5% agarose gel and the amplified DNA-fragments stained with SYBR Green I (Molecular Probes). The fluorescence intensity of the specific bands was visualized and measured by a fluorescence image analyzer (Fluor Imager 575, Molecular Dynamics). The number of male cells in $10^6$ female cells, calculated with a standard curve made from a control amplification of SRY from a standard DNA extracted from $10^6$ female-lymphocytes, is indicated for each tissue noted in FIG. 13.

The result show that FTY720 exerts immunosuppressive activity by sequestering immunologically competent lymphocytes to lymph nodes and Peyer's patches. Also, FTY720 affects the adhesion of lymphocytes to HEV.

EXAMPLE 7

The adhesion of rat lymphocytes to rat high endothelial venule (HEV) cells in vitro.

Rat or mouse HEV cells, such as Ax cells, were plated into 96 well all flat-bottomed microtest plates at a concentration of $1\times10^4$ cells/well, in 100 $\mu$L of RPMI 1640 medium containing 20% fetal calf serum. The cells were cultured for 48 hours to confluency, at 37° C. in an atmosphere of 5% $CO_2$ and 95% air. The lymphocytes prepared from mesenteric lymph nodes and axillary lymph nodes in 7-week old F344 rats or C57BL/6 mice were pre-labeled with calcein-AM at 1 $\mu$mol/L on ice for 30 min. After the labeling with calcein-AM, the lymphocytes were washed three times with ice-cold RPMI 1640 medium. Thereafter, the lymphocytes at $10^6$ cells/well were added to the 96 well microtest plates containing HEV-monolayer in the presence or absence of FTY720 at 1 to 1000 nmol/L. Then, the mixture of the calcein pre-labeled lymphocytes and HEV monolayer were cultured for 120 min at 37° C. in 5% $CO_2$ and 95% air. After incubation, the plates were turned upside down and kept for 30 min to remove HEV-nonadherent cells. Calcein pre-labeled lymphocytes adhered to HEV monolayer were lysed by adding distilled water containing 1% nonidet P-40 and the developed fluorescence was measured at 485/530 nm with fluorescence microplate reader (CytoFluor 2350).

TABLE 1

Effect of FTY720 on adhesion of rat lymphocytes to rat HEV cell lines in vitro.

|  |  | Fluorescence intensity at 485/530 mean ± SE (n = 6) |
|---|---|---|
| Control |  | 1876.2 ± 31.2 |
| FTY720 | 1 nmol/L | 2059.2 ± 112.6 |
|  | 10 | 2107.2 ± 106.5 |
|  | 100 | 2252.0 ± 70.8 |
|  | 1000 | 2383.2 ± 115.2 |

As shown in Table 1, FTY720 at 1 nmol/L or more enhanced the adhesion of calcein-prelabeled lymphocytes to HEV in vitro. Each treatment dose of the ALH-immunosuppressive composition resulted in increased lymphocytes adhering to HEV cells.

TABLE 2

Increase in adhesion of lymphocytes with FTY720-pretreatment of HEV cells but not lymphocytes

| FTY720 Treatment | | Fluorescence intensity at 485/530 |
|---|---|---|
| Lymphocytes | HEV | mean ± SE (n = 6) |
| Experiment 1 | | |
| — | — | 1071.7 ± 342.8 |
| — | 1 nmol/L | 1215.7 ± 191.2 |
| — | 10 | 2926.0 ± 196.4 |
| — | 100 | 2510.2 ± 118.8 |
| Experiment 2 | | |
| — | — | 1967.7 ± 7.8 |
| 100 nmol/L | — | 1945.7 ± 5.2 |

As shown in Table 2, the adhesion of rat lymphocytes to HEV cells was increased by pretreatment of only HEV cells for 3 hours with FTY720 at 1 to 100 nmol/L. By contrast, rat lymphocytes pretreated with FTY720 at 100 nmol/L for 3 hours did not show the acceleration of adhesion to HEV cells. These results suggest that FTY720 acts on HEV cells in lymph nodes and Peyer's patches but not lymphocytes, unlike well-known immunosuppressants.

EXAMPLE 8

Effect of FTY720 on the numbers of lymphocytes in peripheral blood, spleen, mesenteric lymph nodes, and Peyer's patches in vivo.

FTY720 at 0.1 and 1 mg/kg were administered orally to 6 week-old male F344 rats. At 3, 12, 24 hours after administration, peripheral blood, spleen, mesenteric lymph nodes, and Peyer's patches were removed and the lymphocyte numbers of these tissues were measured by using a flow cytometer, as known in the art (EPICS XL). Table 3 shows typical results at 24 hours after the administration.

TABLE 3

Effect of FTY720 on the numbers of lymphocytes in peripheral blood, spleen, mesenteric lymph nodes, and Peyer's patches in vivo.

Number of lymphocytes mean ± SE (cells/μL)

| | | |
|---|---|---|
| Peripheral blood | Control (Vehicle) | 5564.5 ± 422.4 |
| | FTY720 0.1 mg/kg p.o. | 1071.9 ± 59.3** |
| | FTY720 1 mg/kg p.o. | 667.2 ± 199.8** | mean ± SE ($\times 10^5$ cells/tissue)

| | | |
|---|---|---|
| Spleen | Control (Vehicle) | 821.3 ± 85.4 |
| | FTY720 0.1 mg/kg p.o. | 652.3 ± 31.2 |
| | FTY720 1 mg/kg p.o. | 538.0 ± 74.1* | mean ± SE ($\times 10^5$ cells/tissue)

| | | |
|---|---|---|
| Mesenteric lymph nodes | Control (Vehicle) | 245.3 ± 10.0 |
| | FTY720 0.1 mg/kg p.o. | 421.8 ± 27.4** |
| | FTY720 1 mg/kg p.o. | 434.3 ± 33.2** | mean ± SE ($\times 10^4$ cells/tissue)

| | | |
|---|---|---|
| Peyer's patches | Control (Vehicle) | 233.0 ± 36.3 |
| | FTY720 0.1 mg/kg p.o. | 551.5 ± 103.5* |
| | FTY720 1 mg/kg p.o. | 628.8 ± 61.1** |

*$p < 0.05$,
**$p, 0.01$, Dunnett's test (n = 4)

As shown in Table 3, lymphocyte numbers in peripheral blood and spleen decreased after administration of FTY720, in a dose-dependent manner. On the contrary, lymphocyte numbers in mesenteric lymph nodes and Peyer's patches increased significantly after the in vivo treatment with FTY720. These results show that the decrease in the number of lymphocytes in peripheral blood and spleen by FTY720 is due to accelerated lymphocyte homing or migration to mesenteric lymph nodes, peripheral lymph nodes, or Peyer's patches.

EXAMPLE 9
Effect of FTY720 on lymphocyte homing of calcein-prelabeled lymphocytes in various lymphoid tissues.

The lymphocytes prepared from mesenteric lymph nodes and axillary lymph nodes in 5 to 6-week old F344 rats were pre-labeled with calcein-AM (Molecular Probes) at 1 μmol/L on ice for 30 min. After the labeling with calcein-AM, the lymphocytes were washed three times with ice-cold saline. Thereafter, the calcein-prelabeled lymphocytes at $5 \times 10^7$ cells were transfused through the tail vein to sex and age-matched F344 rats. FTY720 at 0.1 or 1 mg/kg was orally administered 2.5 hours before the transfusion. After 30 min. of the transfusion, mesenteric lymph nodes, axillary lymph nodes, Peyer's patches, and spleen were removed and the numbers of calcein prelabeled lymphocytes in these tissues were measured using flow cytometer (EPICS-XL). To examine the influence of antibodies against lymphocyte homing receptors, the calcein-prelabeled lymphocytes were treated with 60 μg/ml of either mouse anti-rat CD49d Mab (clone TA-2) (49), hamster anti-rat CD62L Mab (clone HRL3) (50), mouse anti-rat CD11a Mab (clone WT.1) (51), or control Ig at 4° C. for 30 min. Anti-rat lymphocyte-homing receptor Mabs and control Ig were purchased from Seikagaku-kougyou Ltd. or Pharmingen, respectively.

The results are shown in Tables 4 to 7. FTY720 at an oral dose of 1 mg/kg induced lymphocyte homing of calcein-prelabeled lymphocytes to mesenteric lymph nodes and Peyer's patches. The treatment of anti-CD62L (L-selectin), anti-CD49d (α4-integrin), or anti-CD11a (αL-integrin) antibody significantly inhibited the lymphocyte homing induced by FTY720. Furthermore, FTY720-induced lymphocyte homing was almost completely inhibited by treatment with anti-CD62L antibody, anti-CD49d antibody, and anti-CD11a antibody concomitantly.

These results indicate that FTY720 enhances the lymphocyte homing of peripheral circulating lymphocytes to lymph nodes and Peyer's patches and that FTY720-induced lymphocyte homing is involved in the adhesion of lymphocyte homing receptors, including CD62L, CD49d/beta-7, and CD11a/CD18 (LFA-1), to their ligands (GlyCAM-1, MAdCAM-1, ICAM-1, etc.) expressed on the cell surface of HEV.

TABLE 4

FTY720-induced lymphocyte homing and effect of anti-CD62L antibody on FTY720-induced lymphocyte homing.

| | Lymphocyte homing (Number of calcein-prelabeled lymphocytes) mean ± SE, n = 4 |
|---|---|
| Mesenteric lymph nodes | |
| FTY720 1 mg/kg + Control IgG | 69536 ± 12299 |
| FTY720 1 mg/kg + anti-CD62L antibody | 20577 ± 719* |
| Peyer's patches | |
| FTY720 1 mg/kg + Control IgG | 25929 ± 3575 |
| FTY720 1 mg/kg + anti-CD62L antibody | 3922 ± 672** |

TABLE 5

FTY720-induced lymphocyte homing and effect of anti-CD49d antibody on FTY720-induced lymphocyte homing.

| | Lymphocyte homing (Number of calcein-prelabeled lymphocytes) mean ± SE, n = 4 |
|---|---|
| Mesenteric lymph nodes | |
| FTY720 1 mg/kg + Control IgG | 88350 ± 13629 |
| FTY720 1 mg/kg + anti-CD49d antibody | 34588 ± 3701* |
| Peyer's patches | |
| FTY720 1 mg/kg + Control IgG | 26562 ± 4474 |
| FTY720 1 mg/kg ± anti-CD49d antibody | 5894 ± 471* |

TABLE 6

FTY720-induced lymphocyte homing and effect of anti-CD11a antibody on FTY720-induced lymphocyte homing.

| | Lymphocyte homing (Number of calcein-prelabeled lymphocytes) mean ± SE, n = 4 |
|---|---|
| Mesenteric lymph nodes | |
| FTY720 1 mg/kg + Control IgG | 86021 ± 12961 |
| FTY720 1 mg/kg + anti-CD11a antibody | 47116 ± 3608* |
| Peyer's patches | |
| FTY720 1 mg/kg + Control IgG | 15534 ± 5371 |
| FTY720 1 mg/kg + anti-CD11a antibody | 5894 ± 1707* |

TABLE 7

FTY720-induced lymphocyte homing and effect of anti-lymphocyte antibodies on FTY720-induced lymphocyte homing.

| | Lymphocyte homing mean ± SE, n = 4 |
|---|---|
| | (Number of calcein-prelabeled lymphocytes) |
| Mesenteric lymph nodes | |
| FTY720 1 mg/kg + Control IgG | 62644 ± 3175 |
| FTY720 1 mg/kg + anti-CD62L antibody + anti-CD49d antibody + anti-CD11a antibody | 2019 ± 236** |
| Peyer's patches | |
| FTY720 1 mg/kg + Control IgG | 32822 ± 4191 |
| FTY720 1 mg/kg + anti-CD62L antibody + anti-CD49d antibody + anti-CD11a antibody | 2181 ± 181** |
| | (Number of calcein-prelabeled lymphocytes/10000 cells) |
| Mesenteric lymph nodes | |
| FTY720 1 mg/kg + Control IgG | 167.7 ± 12.5 |
| FTY720 1 mg/kg + anti-CD62L antibody + anti-CD49d antibody | 15.5 ± 4.6** |
| Peyer's patches | |
| FTY720 1 mg/kg + Control IgG | 115.3 ± 1.0 |
| FTY720 1 mg/kg + anti-CD62L antibody + anti-CD49d antibody | 58.6 ± 4.6** |

*$p < 0.05$,
**$p < 0.01$ (Student's t-test)

One skilled in the art will appreciate that various methods and assays designed to identify the presence or absence of lymphocyte homing molecules, receptors, or ligands can also be modified by using the ALH-immunosuppressive compositions of this invention. Furthermore, various treatments to manipulate lymphocyte trafficking and to change or effect lymphocyte levels in tissues of an animal can be made from the description herein. As this example shows, these methods and assays may comprise particular antibodies or binding agents that bind to lymphocyte homing receptors, ligands, or other molecules associated with the lymphocyte homing process. Alternatively, they may involve molecules that interfere with the lymphocyte homing process.

Although the invention has been described and illustrated in detail, one skilled in the art clearly understands that the details are illustrative and exemplary. The details and description should not to be taken as a limitation of the scope of the invention. The spirit and scope of the invention should be limited only by the terms of the appended claims. Furthermore, the description herein enables one skilled in the art to make and use the invention as claimed.

REFERENCES

The disclosure above refers to these references by number. Each of the references is specifically incorporated herein by reference. In addition, one skilled in the art can rely on the contents of these references to make and use embodiments of this invention.

1. Cresswell P, *Ann. R. Immunol.* (1994) 12: 259.
2. Jackson M R, et al., *Ann. R. Cell Biol.* (1993) 9: 207.
3. Howard J C, *Curr. Opin. Immunol.* (1995) 7: 69.
4. Kahan, B D, *N. Eng. J. Med.* (1989) 321: 1725.
5. Fung, J. et al., *Transplant. Proc.* (1991) 23: 2977.
6. Borel, J. F., Feurer, C., Gubler, H. U., and Stahelin, H. The biological effects of cyclosporin A: A new antilymphocytic agent. *Agents and Actions*, 6, 468–475, 1976.
7. Borel, J. F., Pharmacology of cyclosporine (Sandimmune) IV. Pharmacological properties in vivo. *Pharmacological Rev.*, 41, 259–371, 1989.
8. Kino, T., Hatanaka, H., Hashimoto, M., Nishiyama, M., Goto, T., Okuhara, M. Kohsaka, M., Aoki, H., and Imanaka, H. FK-506, a novel immunosuppressant isolated from a Streptomyces I. Fermentation, isolation, and physico-chemical and biological characteristics. *J. Antibiotics*, 40, 1249–1255, 1987.
9. Kino, T., Hatanaka, H., Miyata, S., Inamura, N., Nishiyama, M., Yajima,T., Goto, T., Okuhara, M., Kohsaka, M., Aoki, H., and Ochiai, T. FK-506, a novel immunosuppressant isolated from a Streptomyces II. Immunosuppressive effect of FK-506 in vitro. *J. Antibiotics*, 40, 1256–1265, 1987.
10. Inamura, N. Nakahara, K., Kino, T., Goto, T., Aoki, H., Yamaguchi, I., Kohsaka, M., and Ochiai, T. Prolongation of skin allograft survival in rats by a novel immunosuppressive agent, FK-506. *Transplantation*, 45, 206–209, 1988.
11. Liu, J., Farmer, Jr., J. D., Lane, W. S., Friedman, J., Weissman, I., and Schreiber, S. L. Calcineurin is a common target of cyclophilin-cyclosporin A and FKBP-FK506 complexes. *Cell*, 66, 807–815, 1991.
12. Europian FK506 multicentre liver study group. Randomised trial comparing tacrolimus (FK506) and cyclosporin in prevention of liver allograft rejection. *Lancet.* 344, 423–428, 1994.
13. Slapak. M., Geoghegan, T., Digard, N., Ahmed, K., Sharman, V. L. and Crockett, R. The use of low-dose cyclosporine in combination with azathioprine and steroids in renal transplantaion. *Transplant. Proc.* 17,1 222–1 226, 1985.
14. Kokado, Y., Ishibashi, M., Jiang, H., Takahara, S. and Sonoda, T. Low-dose ciclosporin mizoribine and prednisolone in renal transplantation: a new triple-drug therapy. *Clin. Transplant.*, 4, 191–197, 1990.
15. Fujita, T., Inoue, K., Yamamoto, S., Ikumoto, T., Sasaki, S., Toyama, R., Chiba, K., Hoshino, Y., and Okumoto, T. Fungal metabolites. Part II. A potent immunosuppressive activity found in *Isaria sinclairii* metabolite. *J. Antibiotics*, 47, 208–215, 1994.
16. Sasaki, S., Hashimoto, R., Kiuchi, M., Inoue, K., Ikumoto, T., Hirose, R., Chiba, K., Hoshino, Y., Okumoto, T., and Fujita, T. Fungal metabolites. Part 14. Novel potent immunosuppressants, mycestericins, produced by *Myceria sterilia. J. Antibiotics*, 47, 420–433, 1994.
17. Fujita, T., Inoue, K., Yamamoto, S., Ikumoto, T., Sasaki, S., Toyama, R., Yoneta, M., Chiba, K., Hoshino, Y., and Okumoto, T. Fungal metabolites. Part 12. Potent immunosuppressant, 14-deoxomyriosin, (2S,3R,4R)-(E)-2-amino-3,4-dihydroxy-2-hydroxymethyleicos-6-enoic acid and structure-activity relationships of myriocin derivatives. *J. Antibiotics*, 47, 216–224, 1994.
18. Fujita, T., Yoneta, M., Hirose, R., Sasaki, S., Inoue, K., Kiuchi, M., Hirase, S., Adachi, K., Arita, M., and K. Chiba. Simple compounds, 2-alkyl-2amino-1,3-propanediols have potent immunosuppressive activity. *BioMed. Chem. Lett.*, 5, 847–852, 1995.
19. Fujita, T., Hirose, R., Yoneta, M., Sasaki, S., Inoue, K., Kiuchi, M, Hirase, S., Chiba, K., Sakamoto, H., and Arita, M. Potent immunosuppressants, 2-alkyl-2-aminopropane-1,3-diols. *J. Med. Chem.*, 39, 4451–4459, 1996.
20. Adachi, K., Kohara, T., Nakao, N., Arita, M., Chiba, K., Mishina, T., Sasaki,S., and Fujita, T. Design, synthesis, and structure activity relationships of 2-substituted-2-amino-1,3-propanediols: Discovery of a novel 21. Chiba, K., Hoshino, Y., Suzuki, C., Masubuchi, Y., Yanagawa, Y., Ohtsuki, M., Sasaki, S., and Fujita, T. FTY720, a novel immunosuppressant possessing unique mechanisms. I. Prolongation of skin allograft survival and synergistic effect in combination with cyclosporine in rat. *Transplant Proc.*, 28;1056–1059, 1996.
22. Kahan, B. D., Tejpal, N., Stubbers, S. G., Tu, Y., Wang, M., Stepkowski, S. and Chou, T. C. The synergistic interactions in vitro and in vivo of brequinar sodium with cyclosporine or rapamycin alone and in triple combination. *Transplantation*, 55, 894–900, 1993.
23. Hoshino, Y., Suzuki, C., Masubuchi, M., Amano, Y., and Chiba, K. FTY720, a novel immunosuppressant possessing unique mechanisms.11. Long-term graft survival induction in rat heterotopic cardiac allograft and synergistic effect in combination with cyclosporine A. *Transplant Proc.*, 28, 1060-1061, 1996.
24. Kawaguchi, T., Hoshino, Y., Rahman, F., Amano, Y., Higashi, H., Kataoka, H., Ohtsuki, M., Teshima, K., Chiba, K., Kakefuda, T., and Suzuki, S. FTY720, a novel immunosuppressant possessing unique mechanisms.111. Synergistic prolongation of canine renal allograft survival in combination with cyclosporine A. *Transplant. Proc.*, 28, 1062-1063, 1996.
25. Suzuki, S., Enosawa, S., Kakefuda, T., Shinomiya, T., Amari, M., Naoe, S., Hoshino, Y., and Chiba. K. A novel immunosuppressant, FTY720, having an unique mechanism of action induces long-term graft acceptance in rat and dog allotransplantation. *Transplantation*, 61, 200–205, 1996.
26. Suzuki, S., Enosawa, S., Kakefuda, T., Amamiya, H., Hoshino, Y., and Chiba, K. Long-term graft acceptance in allografted rats and dogs by treatment with a novel immunosuppressant, FTY720. *Transplant. Proc.*, 28, 1375-1376, 1996.
27. Davies, Hff. S., Collier, D. St. J., Thiru, S., Decurtins, M. and Caine, R. Y. Long-term survival of kidney allografts in dogs after withdrawal of immunosuppression with ciclosporin and azathioprine. *Eur. Surg. Res.*, 21, 65–75, 1989.
28. Amemiya, H., Suzuki, S., Niiya, S., Watanabe, H., and Kotake, T., Synergistic effect of cyclosporine and mizoribine on survival of dog renal allografts. *Transplantation*, 46, 768–771, 1988.
29. Masubuchi, Y., Kawaguchi, T., Ohtsuki, M., Suzuki, C., Amano, Y., Hoshino, Y., and Chiba, K. FTY720, a novel immunosuppressant possessing unique mechanisms. IV. Prevention of graft versus host reactions in rats. *Transplant. Proc.*, 28, 1064-1065, 1996.
30. Arbones, M. L., Ord, D. C., Ley, K., Ratech, H., Curry, C. M., Otten, G., Capon, D. J., and Tedder, T. F. Lymphocyte homing and leukocyte rolling and migration are impaired in L-slectin-deficient mice. *Immunity*, 1, 247–260, 1994.
31. Hamann, A., Andrew, D. P., Westrich, D. J. Holzmann, B., and Butcher, E. C. Role of c4-integrins in lymphocyte homing to mucosal tissue in vivo. *J. Immunol.*, 152, 3282–3293, 1994.
32. Imai Y., Lasky, L. A. and Rosen, S. D. Sulphation requirement for GlyCAM-1, an endothelial ligand for L-selectin. *Nature*, 361, 555–557, 1993.
33. Berlin, C., Berg, E. L., Briskin, M. J., Andrew, D. P., Kilshaw, P. J., Holzmann, B., Weissman, I. L., Hamann, A., and Butcher, E. C. $\alpha_4\beta_7$ integrin mediates lymphocyte binding to the mucosal vascular addressin MAdCAM-1. *Cell*, 74, 185–195, 1993.
34. Kahan, B D, *Transplantation* (1991) 52: 185.
35. Schwartz, R S et al., *Nature* (1959) 183: 1682.
36. Turka, L A et al., *J. Clin. Invest.* (1991) 87: 940.
37. Lee, W A et al., *Pharm. Res.* (1990) 7: 161.
38. Cramer, D V et al., *Transplantation* (1992) 53: 303.
39. Picker, L J et al., Physiological and molecular mechanisms of lymphocyte homing. *Ann. Rev. Immunol.* (1992) 10; 561.
40. Miller et al., *Transplantation* (1987) 39: 555.
41. Dallman M J, et al., *Immunol. Rev.* (1991) 119: 163.
42. Dallman M J, et al., (1991) *J. Exp. Med.* 174: 493.
43. Wang, J et al., *Science* (1997) 275: 1937; Shanahan, F, Science (1997) 275: 1897.
44. A. Siegling, M. Lehmann, C. Platzer, F. Emmrich, and H.-D. Volk. A novel multiple competitor fragment for quantitative PCR analysis of cytokine gene expression in rats. *J. Immunol. Methods* (1994) 177: 23–28.
45. T. Tanaka, T. Masuko, H. Yagita, T. Tamura, and Y. Hashimoto, Characterization of a CD3-like rat T cell surface antigen recognized by a monoclonal antibody. *J. Immunol.* (1989) 142: 2791–2795.
46. G. R. Woollett, A. N. Barclay, M. Puklavec and A. F. Williams, Molecular and antigenic heterogeneity of the rat leukocyte-common antigen from thymocytes and T and B lymphocytes. *Eur. J. Immunol.* (1985) 15: 168–173.
47. Y. Masaki, A. Hirasawa, S. Okuyama, G. Tsujimoto, M. lwaya, X-K. Li, Y. Yokoi, S. Nakamura, S. Baba, Miyamoto, M. Hara, K Shibata. Y Koga, H. Amemiya, and H. Kimura, Microchimerism and heart allograft acceptance. *Transplant. Proc.* (1995) 27: 148.
48. C. Legendre, H. Kreis, J. F. Bach, and L. Chatenoud, Prediction of successful allograft rejection retreatment with OKT3. *Transplantation* (1992) 53: 94–94; other immunosuppressive and/or anti-lymphocyte antibodies are known in the art, for example, McEvoy, L. M., Sun, H., Frelinger, F. G., and Butcher, E. C., Anti-CD43 anhibition of T cell homing. *J. Exper. Med.* (1997) 185: 1493–1498.
49. T. Tamatani, F. Kitamura, K.Kuida, M. Shirao, M. Mochizuki, M. Suematsu, G. W. Schmid-Schonbein, K. Watanabe, S, Tsurufuzi and M. Miyasaka, Characterization of rat LECAM-1 (L-selectin) by the use of monoclonal antibodies and evidence for the presence of soluble LECAM-1 in rat sera. *Eur. J. Immunol.* 23, 2181–2188 (1993).
50. T. B. Issekatz, Inhibition of in vivo lymphocyte migration to inflammation and homing to lymphoid tissues by TA-2 monoclonal antibody, *J Immunol.*, 147, 4178–4184 (1991).
51. T. Tamatani, M. Kotani, and Miyasaka, M., Characterization of the rat leukocyte integrin, CD11/CD18, by the use of LFA-1 subunit-specific monoclonal antibodies. *Eur. J Immunol.* 21, 627–633 (1991).

What is claimed is:

1. A method for accelerating the lymphocyte homing activity of the immune system of a mammal, while simultaneously maintaining the IL-2 mRNA expressing ability of T cells in the mammal, comprising introducing an effective amount of an accelerated lymphocyte homing composition comprising 2-amino-2[2-(4-octylphenyl)ethyl]propane-1,3-diol hydrochloride to the mammal.

2. A method for reversibly reducing the number of circulating lymphocytes in a mammal other than rat or dog, comprising introducing an effective amount of an accelerated lymphocyte homing composition comprising 2-amino-2[2-(4-octylphenyl)ethyl]propane-1,3-diol hydrochloride or to the mammal, wherein a measurable amount of the circulating lymphocytes are directed to peripheral or mesenteric lymphoid tissue.

3. A method of manipulating lymphocyte traffic in a mammal comprising administering a composition comprising an effective amount of an accelerated lymphocyte homing compound comprising 2-amino-2[2-(4-octylphenyl)ethyl]propane-1,3-diol hydrochloride.

4. The method according to claim 1, wherein the lymphocyte homing is to mesenteric or peripheral lymphoid tissue.

5. The method according to claim 1, wherein the lymphocyte homing is to Peyer's patches.

6. The method according to claim 1, wherein the introducing is by oral administration.

* * * * *

UNITED STATES PATENT AND TRADEMARK OFFICE
CERTIFICATE OF CORRECTION

PATENT NO. : 6,004,565
DATED : December 21, 1999
INVENTOR(S) : Chiba et al.

It is certified that error appears in the above-indentified patent and that said Letters Patent is hereby corrected as shown below:

In the DRAWINGS:

Add Figure 10.

In the SPECIFICATION:

Col. 1, line 66, change "TRUFKBP" to --TRL/FKBP--.
Col. 2, line 3, change "TRUFKBP" to --TRL/FKBP--.
Col. 4, line 2, change "akylamino" to --alkylamino--.
Col. 4, line 34, change "of" to --or--.
Col. 9, line 19, change "creatine" to --creatinine--.
Col. 9, line 47, change "GsA" to --CsA--.
Col. 13, line 45, change "RT1k" to --$RT1^k$.--
Col. 14, lines 39-40, change "creatine" to --creatinine--.
Col. 14, line 42, change "creatine" to --creatinine--.
Col. 15, line 45, delete "nLn".
Col. 15, line 50, delete "and".
Col. 17, line 47, delete "all".
Col. 20, line 43, change "13629" to --13029--.
Col. 21, line 29, change "4.6" to --4.7--.

UNITED STATES PATENT AND TRADEMARK OFFICE
CERTIFICATE OF CORRECTION

PATENT NO.    : 6,004,565
DATED         : December 21, 1999
INVENTOR(S)   : Chiba et al It is certified that error appears in the above-identified patent and that said Letters Patent is hereby corrected as shown below:

IN THE CLAIMS:

Col. 25, line 5, delete "or".

Signed and Sealed this

Twenty-fourth Day of April, 2001

Attest:

NICHOLAS P. GODICI

Attesting Officer

Acting Director of the United States Patent and Trademark Office